(12) United States Patent
Mueller et al.

(10) Patent No.: US 11,058,568 B2
(45) Date of Patent: *Jul. 13, 2021

(54) KNEE BRACE

(71) Applicant: Mueller Sports Medicine, Inc., Prairie du Sac, WI (US)

(72) Inventors: Brett Mueller, Middleton, WI (US); Zhaodong Max Li, Lodi, WI (US); Keith Kusmirek, Madison, WI (US)

(73) Assignee: Mueller Sports Medicine, Inc., Prairie du Sac, WI (US)

(*) Notice: Subject to any disclaimer, the term of this patent is extended or adjusted under 35 U.S.C. 154(b) by 201 days.

This patent is subject to a terminal disclaimer.

(21) Appl. No.: 16/113,733

(22) Filed: Aug. 27, 2018

(65) Prior Publication Data

US 2018/0360638 A1 Dec. 20, 2018

Related U.S. Application Data

(63) Continuation of application No. 14/750,949, filed on Jun. 25, 2015, now Pat. No. 10,058,446, which is a continuation-in-part of application No. 14/192,713, filed on Feb. 27, 2014, now Pat. No. 9,254,215.

(60) Provisional application No. 61/771,228, filed on Mar. 1, 2013, provisional application No. 61/770,926, filed on Feb. 28, 2013, provisional application No. 62/016,750, filed on Jun. 25, 2014, provisional application No. 62/016,765, filed on Jun. 25, 2014.

(51) Int. Cl.
*A61F 5/01* (2006.01)
*A61F 5/30* (2006.01)

(52) U.S. Cl.
CPC .......... *A61F 5/0123* (2013.01); *A61F 5/0106* (2013.01); *A61F 5/0109* (2013.01); *A61F 5/30* (2013.01)

(58) Field of Classification Search
CPC .... A61F 5/0104; A61F 5/0106; A61F 5/0109; A61F 5/0118; A61F 5/0123; A61F 5/013; A61F 5/30
USPC .................................. 602/20, 23, 26, 60–63
See application file for complete search history.

(56) References Cited

U.S. PATENT DOCUMENTS

| | | | | |
|---|---|---|---|---|
| 5,472,413 A * | 12/1995 | Detty | ................. | A41D 13/0568 2/16 |
| 9,254,215 B2 * | 2/2016 | Mueller | ................ | A61F 5/0109 |
| 9,827,132 B2 * | 11/2017 | Mueller | ................ | A61F 5/0118 |
| 10,058,446 B2 * | 8/2018 | Mueller | ................ | A61F 5/0109 |
| 2008/0255494 A1 * | 10/2008 | Rousso | ................. | A61K 31/44 602/62 |

* cited by examiner

*Primary Examiner* — Keri J Nelson
(74) *Attorney, Agent, or Firm* — Rick L. Abegglen

(57) ABSTRACT

A knee brace for use by athletes or others requiring protection and support of the knee. The knee brace includes a base and a spider member. The base is comprised of elastic material and configured to closely fit around portions of the knee and adjacent leg portions. A spider member having upper and lower pairs of tensioning straps is fastened to the interior surface of the base, with the tensioning straps extending through upper and lower apertures in the base for detachable attachment to the exterior surface of the base.

20 Claims, 23 Drawing Sheets

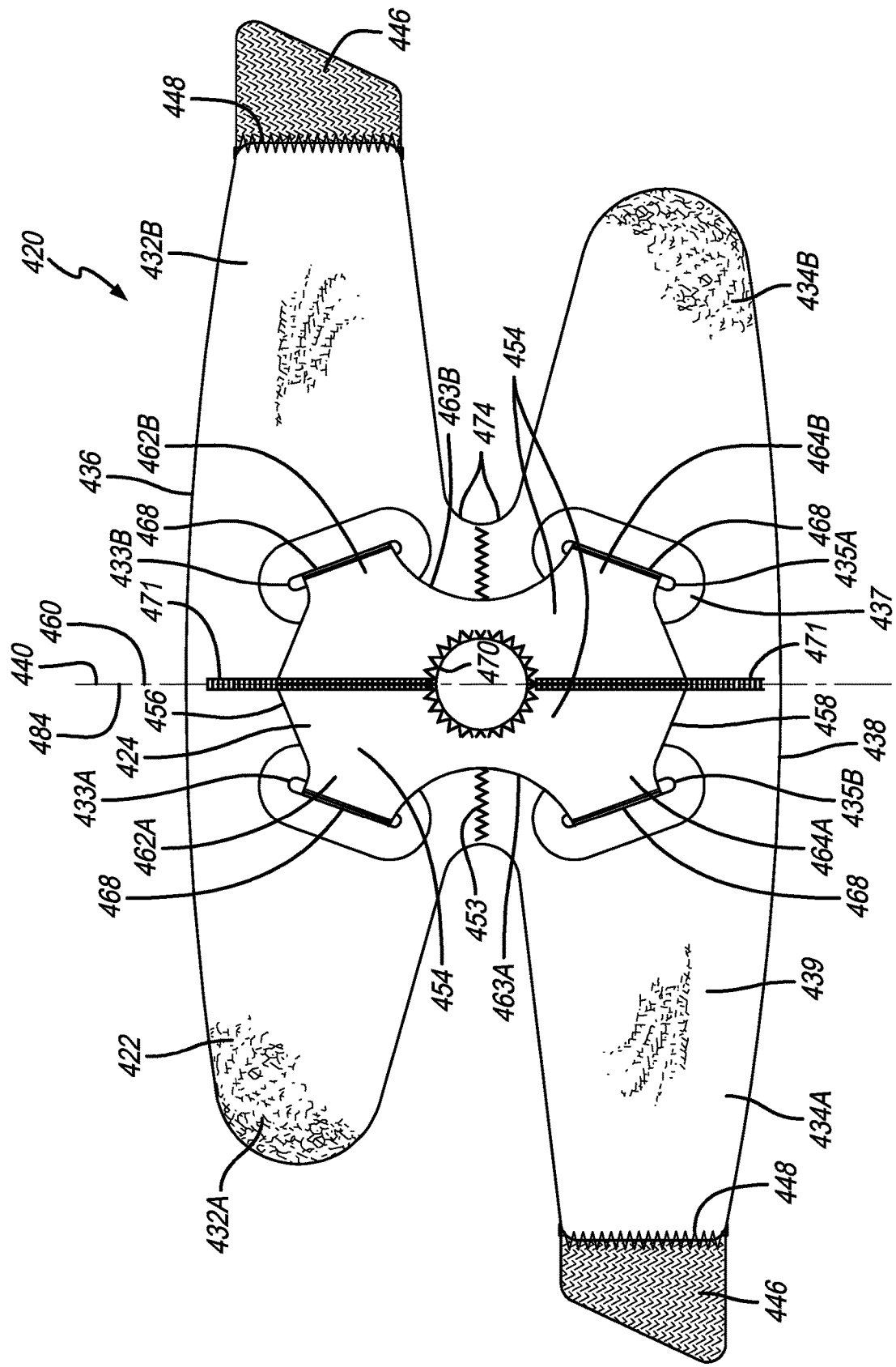

KNEE BRACE

CROSS REFERENCE TO RELATED APPLICATIONS

This application is a continuation of application Ser. No. 14/750,949 filed Jun. 25, 2015 and now pending (which claims priority to provisional application No. 62/016,750 filed Jun. 25, 2014 and provisional application No. 62/016,765 filed Jun. 25, 2014) and is a continuation-in-part of application Ser. No. 14/192,713 filed Feb. 27, 2014 (which claims priority to provisional application No. 61/771,228 filed Mar. 1, 2013 and provisional application No. 61/770,926 filed Feb. 28, 2013). Each of the patent applications identified above is incorporated here by reference in its entirety for continuity of disclosure.

FIELD OF THE INVENTION

This invention relates generally to the field of articles worn by persons to reduce the likelihood, severity, or exacerbation of injury to the body, and more specifically to the field of braces worn on the knee.

BACKGROUND OF THE INVENTION

Flexible knee braces are used by athletes and other persons engaged in vigorous physical activity to protect the knee from injury and to avoid exacerbation of existing injury. The knee is one of the most heavily used joints of the body, as it is used in any activity that involves walking or running. The knee is also a common subject of injury, due to the relatively high levels of stress it must bear. During normal ambulation, in occupations involving physical labor, and especially during strenuous sports, the knee can undergo abnormal motions as a result of quick changes in direction, fatigue, uneven surfaces, or impacts. These abnormal motions can cause sprains or more serious injuries, including dislocation, stretching, or tearing of the tissues that make up the knee.

Several different types of abnormal motion can cause injury to the knee. First, hyperextension of the knee joint can occur, wherein the knee flexes in its normal front to back fashion but beyond its normal range of motion. A second type of abnormal motion is axial rotation, wherein the lower leg is twisted rotationally relative to the thigh about the knee joint. A third type of abnormal motion is lateral flexure of the lower leg relative to the thigh, wherein the knee joint flexes from side to side instead of the normal front to back motion. In addition, abnormal motion of the patella (kneecap) can result in injuries such as chondromalacia patella, which is a softening or degeneration of the undersurface of the patella, and dislocation of the patella, also known as subluxation of the patella.

Devices to protect the knee against abnormal motions have been used for many years, in a variety of specific embodiments which vary in their abilities to protect against the different types of abnormal motions. Besides protecting the knee against abnormal motions, the devices sometimes provide additional benefits such as insulating the knee to keep it warm, protecting the knee against impact, or compressing the knee to reduce discomfort. However, the protections afforded by these devices against abnormal motion are often accompanied by a reduction in range or ease of normal motion. These devices can also have other undesirable aspects such as added weight on the leg, potential for self-injury or injury to others caused by rigid components, difficulty of application and removal, cost, appearance, and irritation or chafing of the skin.

For these reasons, there has long been motivation to find an improved knee brace which can protect the knee from abnormal motions without affecting the range or ease of normal motion, while avoiding the undesirable aspects of prior art devices.

SUMMARY OF THE INVENTION

In a first embodiment, a knee brace according to the present invention includes a base and a spider member having pairs of upper and lower tensioning straps, wherein the spider member is permanently fastened to the interior surface of the base.

According to another aspect of the invention, a knee brace according to the present invention includes a base and a spider member having pairs of upper and lower tensioning straps, wherein the spider member is permanently fastened to the base by a plurality of stitches through the mid-line axes of the base and spider member.

According to another aspect of the invention, a knee brace according to the present invention includes a base with pairs of upper and lower apertures, and a spider member positioned between the base and the leg of the person when worn and having pairs of upper and lower tensioning straps, wherein the tensioning straps extend through the apertures in the base when the brace is worn.

In a second embodiment, a knee brace according to the present invention includes a base, and a shaped tensioning member formed of a synthetic fiber that is relatively elastic in all directions, for example of the type known as spandex in the United States or elasthane, or sold under the trademark LYCRA®, although this is not required and other materials could be used. The tensioning member is permanently fastened to the interior surface of the base and has free ends extending through apertures in the base where they can be fastened to the exterior surface of the base using hook-and-loop fastening material. In a third embodiment, one or more resilient stays can also be provided for additional support.

In a fourth embodiment, a knee brace according to the present invention includes a base, an external mesh layer, and a multi-part internal spider member comprising a shaped tensioning member formed of a synthetic fiber that is relatively elastic in all directions, for example, of material of the type known as spandex in the United States or elasthane, or sold under the trademark LYCRA®, although this is not required and other materials could be used. The shaped tensioning member has a central portion that is permanently fastened to the interior surface of the base, and has straps extending through apertures in the base to (free) strap ends that are fastenable to the exterior surface of the base using hook-and-loop fastening material. The straps may include inelastic portions, for example near the second (free) ends.

In a fifth embodiment, a knee brace according to the present invention includes a base, an external mesh layer, and upper and lower crossed straps formed of a synthetic fiber that is relatively elastic in all directions, for example, of material of the type known as spandex in the United States or elasthane, or sold under the trademark LYCRA®, although this is not required and other materials could be used. The crossed straps have first ends permanently fastened to the interior surface of the base and extending through apertures in the base to second (free) ends that are fastenable to the exterior surface of the base using hook-and-loop fastening material. The straps may include inelastic portions, for example near the second (free) ends.

Inelastic portions of the straps can be formed by simply substituting elastic material with inelastic material at the locations where an inelastic portion is desired, for example extending from a location near the aperture when worn to the free ends. Alternatively, an inelastic portion can be formed by sandwiching and/or overlapping portions of the elastic material with an additional layer of inelastic material straps. If overlapped or sandwiched, one side of the resulting sandwich can be left open to form a pocket to hold small items such as keys, access fobs, ID or credit cards, smart devices (for example fitness trackers) or visible flair such as brightly colored items, reflectors, blinking lights, glow sticks, or other lighting. In such a case the external mesh layer is preferably made of a mesh or other transparent or translucent material to allow the flair or lighting to be seen. One or more reflective patches can also be provided to enhance visibility of the wearer.

Further objects, features, and advantages of the invention will be apparent from the following detailed description when taken in conjunction with the accompanying drawings.

BRIEF DESCRIPTION OF THE DRAWINGS

In the drawings:

FIG. 7B is a plan view of the knee brace of FIG. 7A, laid flat to expose the interior surface of the brace;

DETAILED DESCRIPTION OF THE INVENTION

Figure 1A:
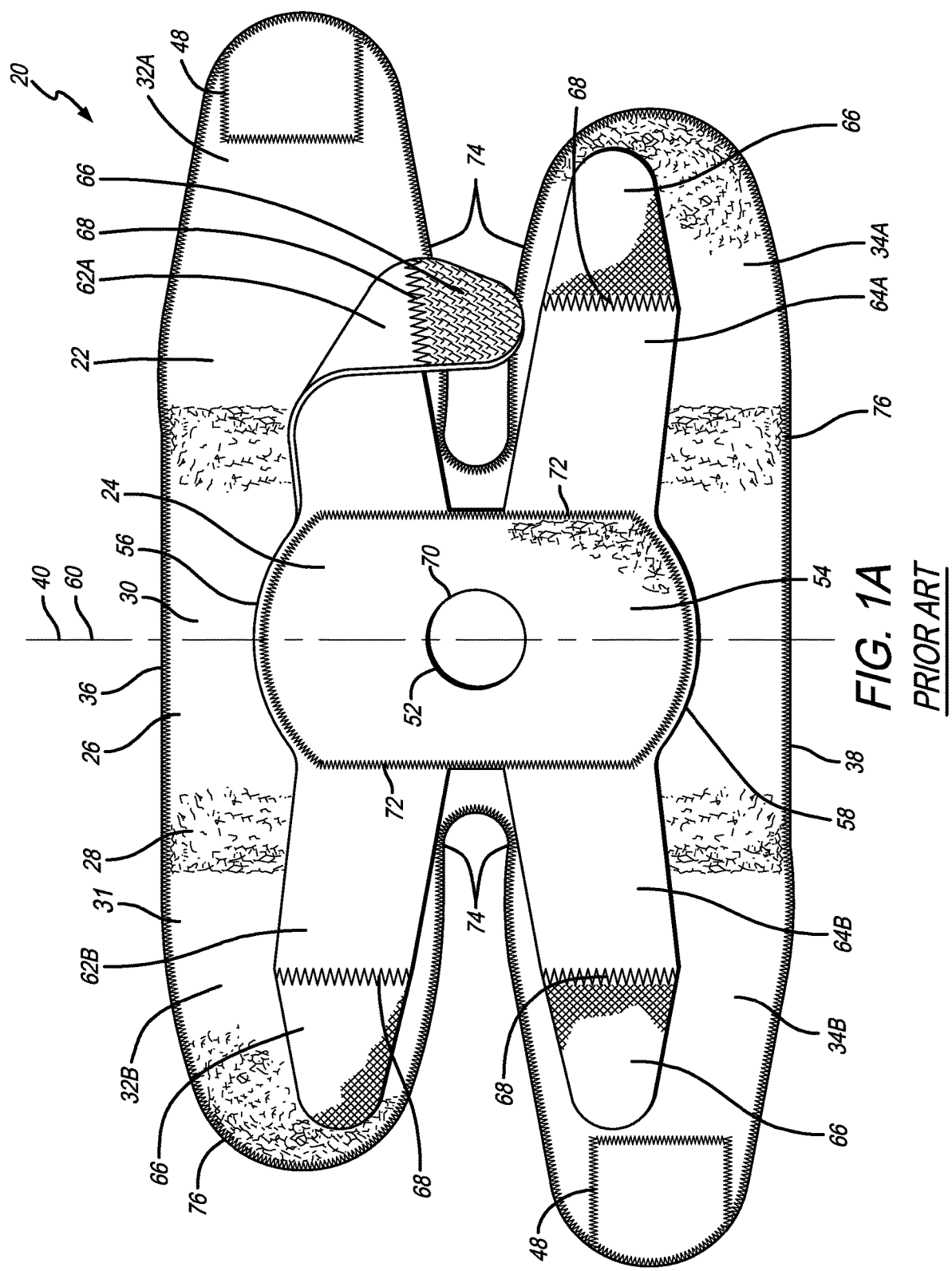
FIG. 1A is a plan view of a prior art knee brace, laid flat to expose the exterior surface of the brace.
Figure 1B:
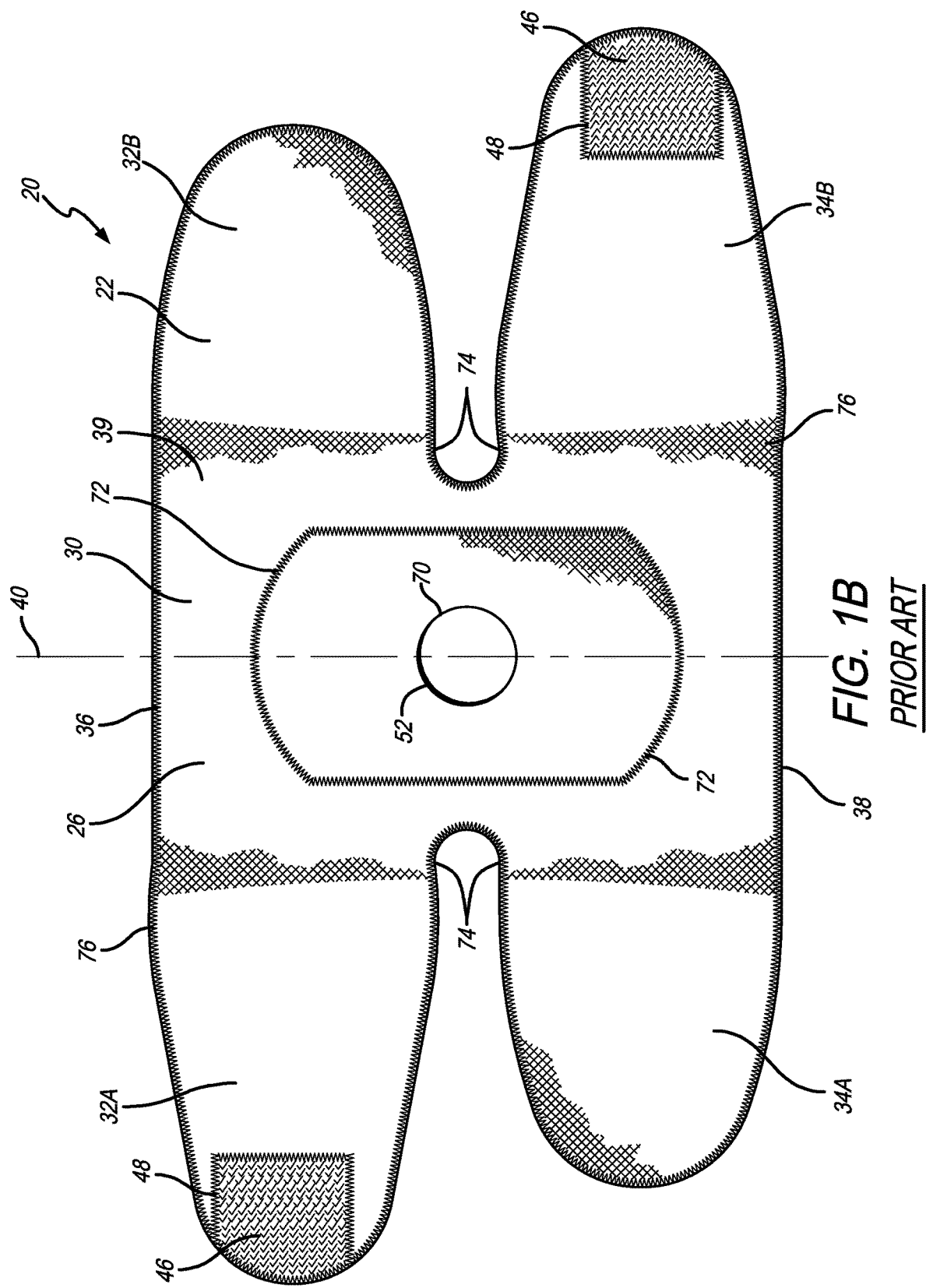
FIG. 1B is a plan view of the prior art knee brace of FIG. 1A, laid flat to expose the interior surface of the brace.

Referring to the drawings, FIGS. 1A and 1B show a prior art knee brace 20, similar to the design taught in U.S. Pat. No. 5,472,413, the contents of which are hereby incorporated by reference. The prior art knee brace 20 includes a base member 22 and a spider member 24, each made by cutting planar sheets 26 of an elastomeric material into the desired shapes. The exterior surface 31 of the base member 22 is preferably covered with fabric bearing fiber loops 28 that adheres to hook-type material when the fiber loops and hook-type material are pressed together.

The base 22 of the prior art knee brace 20 has a base central portion 30 extending vertically from an upper edge 36 to a lower edge 38, and has a mid-line axis 40 running vertically down the middle of base central portion 30. The base 22 includes a first upper mounting strap 32A, a second upper mounting strap 32B, a first lower mounting strap 34A, and a base second lower mounting strap 34B extending from the central portion 30.

As perhaps best shown in FIG. 1B which shows the interior surface 39 of the base 22, the first upper mounting strap 32A and first lower mounting strap 34A terminate in hook-type strap fastening tabs 46 suitable for detachable attachment to the fabric bearing fiber loops 28 on the exterior surface 31 of the base member 22. The strap fastening tabs 46 are sewn to the mounting straps with stitches 48.

The base also has a kneecap opening 52 to receive the kneecap when the brace is worn, it may be formed to include a recess 74 to prevent bunching when the brace is worn, and the base preferably includes edge binding 76, although none of these features are required.

As perhaps best shown in FIG. 1A which shows the exterior surface 31 of the base 22, the prior art knee brace 20 includes a spider member 24. The spider member 24 has a spider member central portion 54 extending vertically from an upper edge 56 to a lower edge 58, and has a mid-line axis 60 running vertically down the middle of the spider member central portion 54. The spider member 24 is permanently attached to the exterior surface 31 of the base 22 by stitches 72 that extend around the periphery of the spider member central portion 54.

The spider member 24 includes a first upper tensioning strap 62A, a second upper tensioning strap 62B, a first lower tensioning strap 64A, and a second lower tensioning strap 64B extending from the central portion 54. Each of the tensioning straps 62A, 62B, 64A, 64B terminates in hook-type fastening tabs 66 suitable for detachable attachment to the fabric 28 on the exterior surface of the base 22 and sewn to the tensioning straps with stitches 68. The spider member 24 also has a kneecap opening 70 to receive the kneecap when the brace is worn.

Figure 2A:
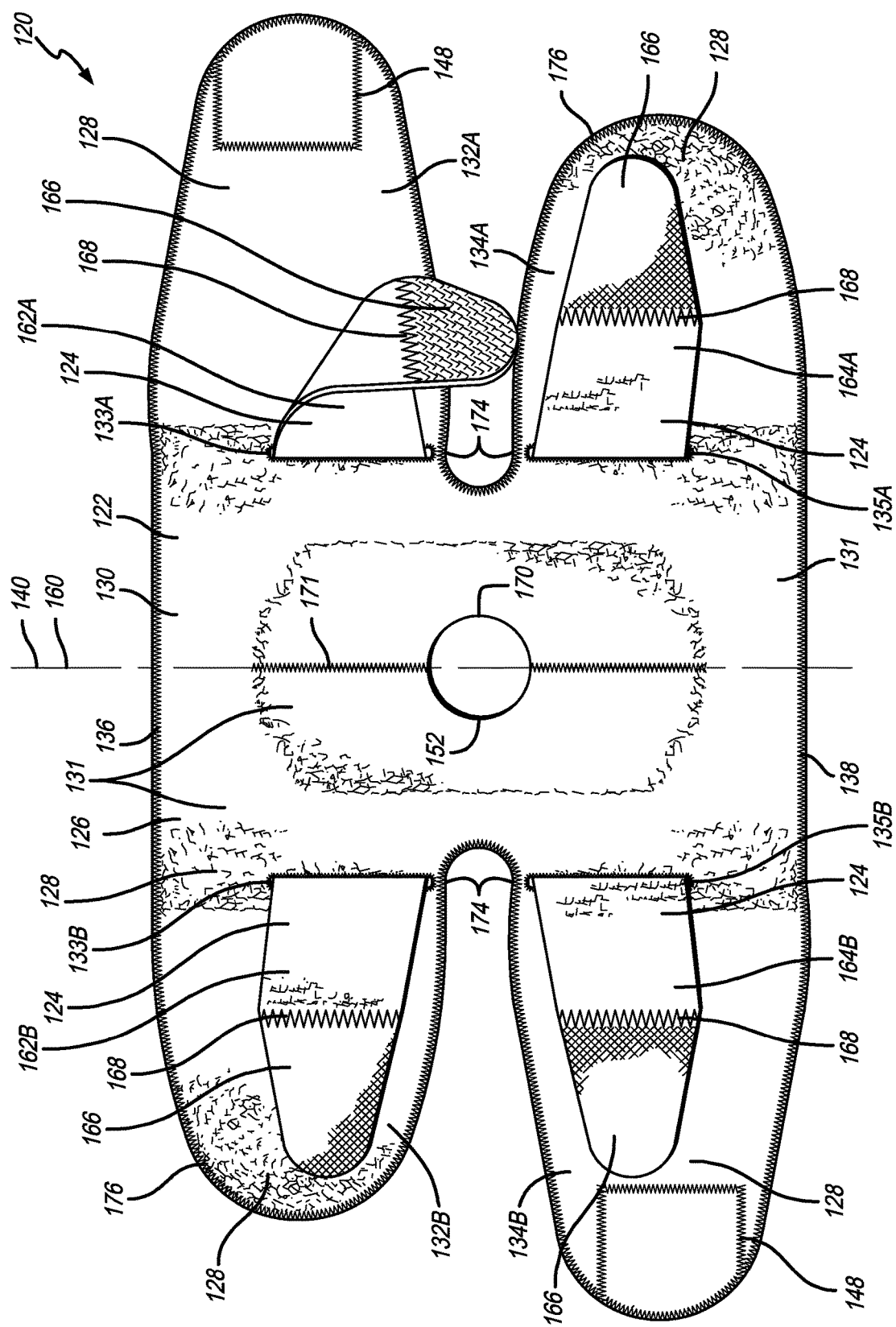
FIG. 2A is a plan view of a first embodiment of a knee brace according to the present invention, laid flat to expose the exterior surface of the brace.
Figure 2B:
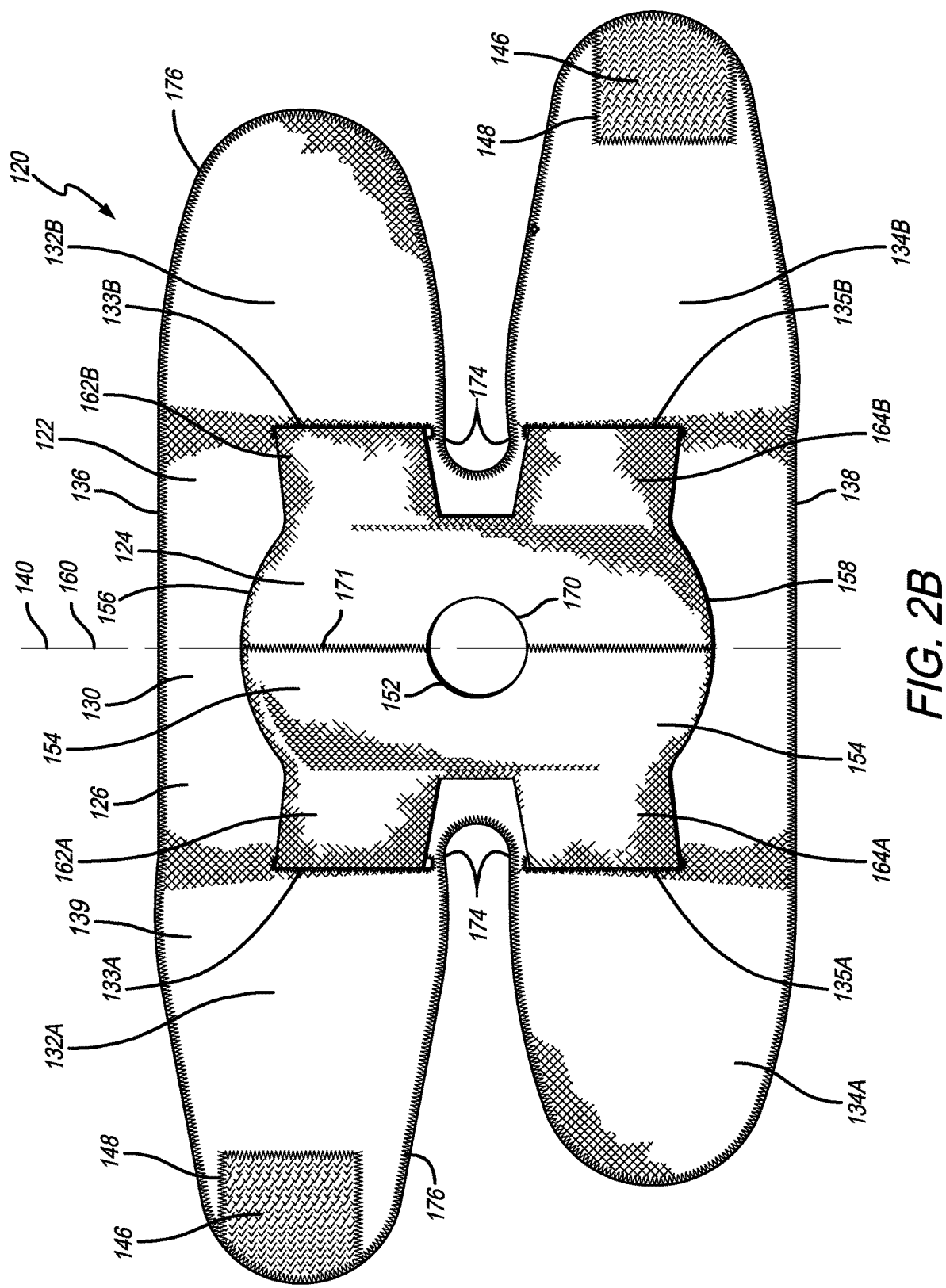
FIG. 2B is a plan view of the knee brace of FIG. 2A, laid flat to expose the interior surface of the brace.
Figure 3A:
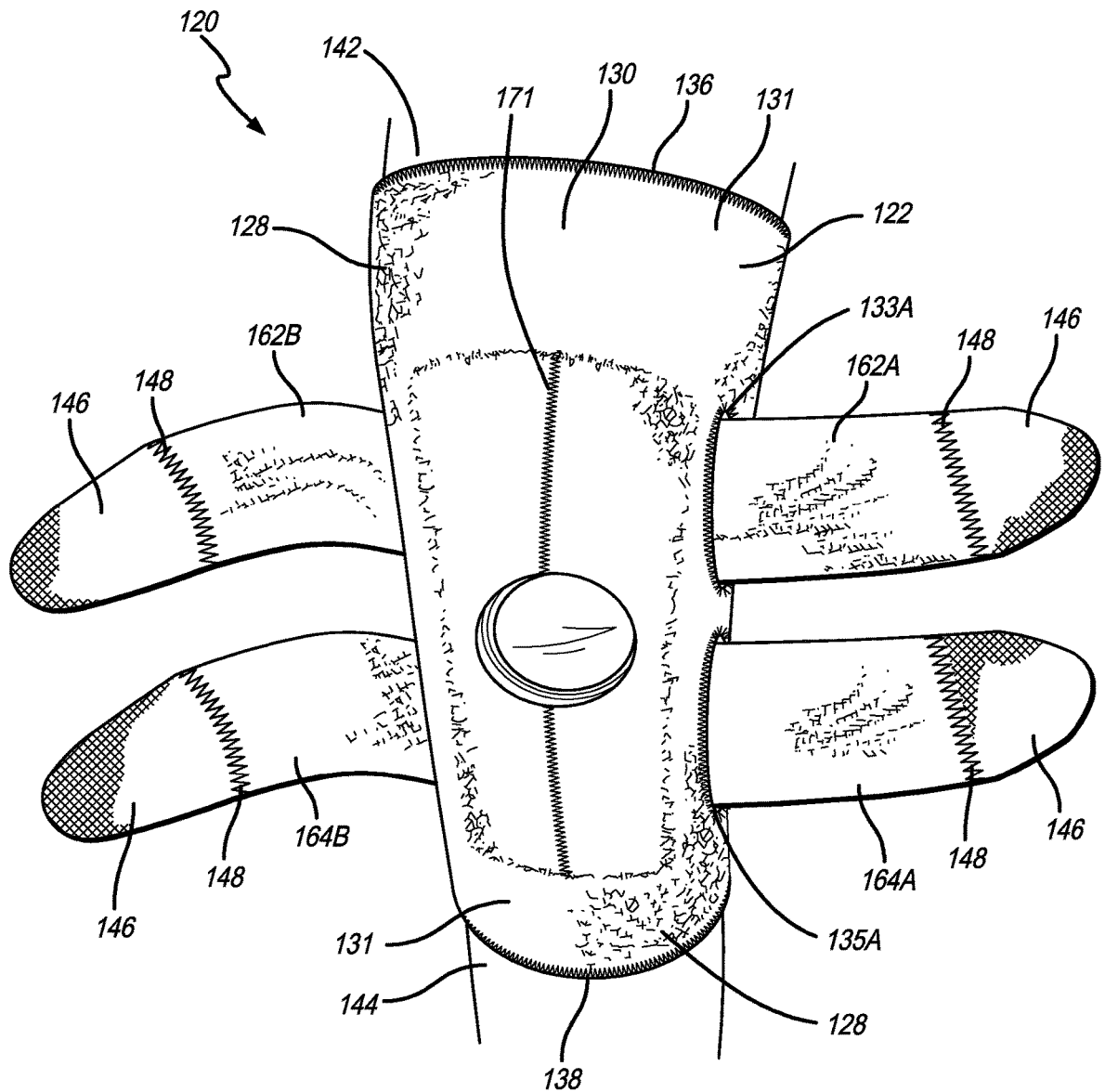
FIG. 3A is a front view of the knee brace of FIGS. 2A-2B, applied to the leg of a person with the base mounting straps fastened, but with the spider straps unfastened.
Figure 3B:
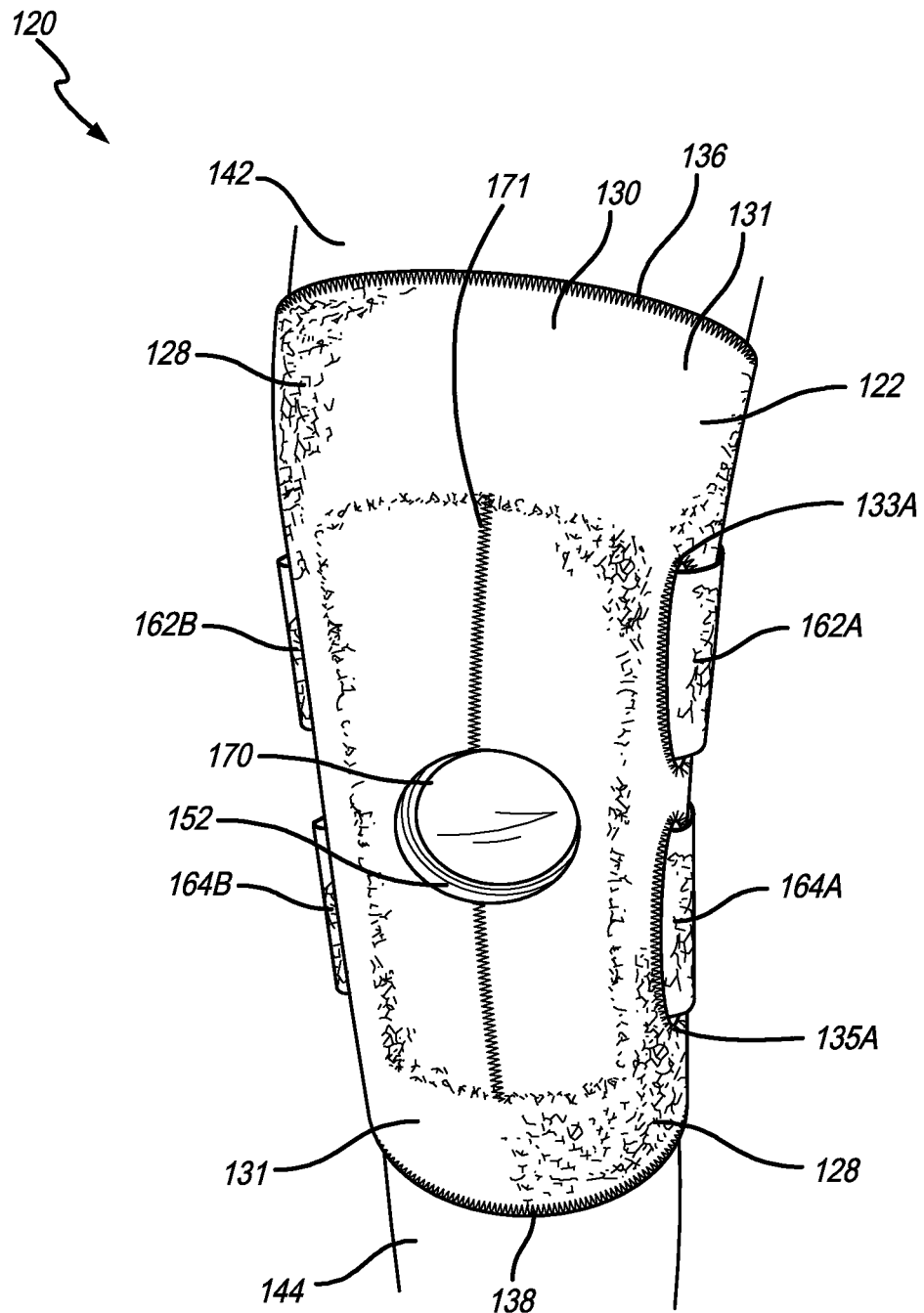
FIG. 3B is a front view of the knee brace of FIGS. 2A-2B, applied to the leg of a person with the base mounting straps fastened, and with the spider straps fastened as well.

FIGS. 2A and 2B show exterior and interior plan views, respectively, of a knee brace 120 according to the present invention laid flat. The knee brace 120 includes a base member 122 and a spider member 124, each made by cutting planar sheets 126 of an elastomeric material into the desired shapes. The outer surface of the base member 122 is preferably covered with fabric bearing fiber loops 128 that adheres to hook-type material when the fiber loops and hook-type material are pressed together.

The base 122 of the knee brace 120 has a base central portion 130 extending vertically from an upper edge 136 to a lower edge 138, and has a mid-line axis 140 running vertically down the middle of base central portion 130. The base 122 includes a first upper mounting strap 132A, a second upper mounting strap 132B, a first lower mounting strap 134A, and a base second lower mounting strap 134B extending from the central portion 130.

As perhaps best shown in FIG. 2B which shows the interior surface 139 of the base 122, the first upper mounting strap 132A and first lower mounting strap 134A terminate in hook-type strap fastening tabs 146 suitable for detachable attachment to the fabric bearing fiber loops 128 on the external surface 131 of the base 122. The hook-type strap fastening tabs 146 are sewn to the mounting straps with stitches 148.

Figure 4A:
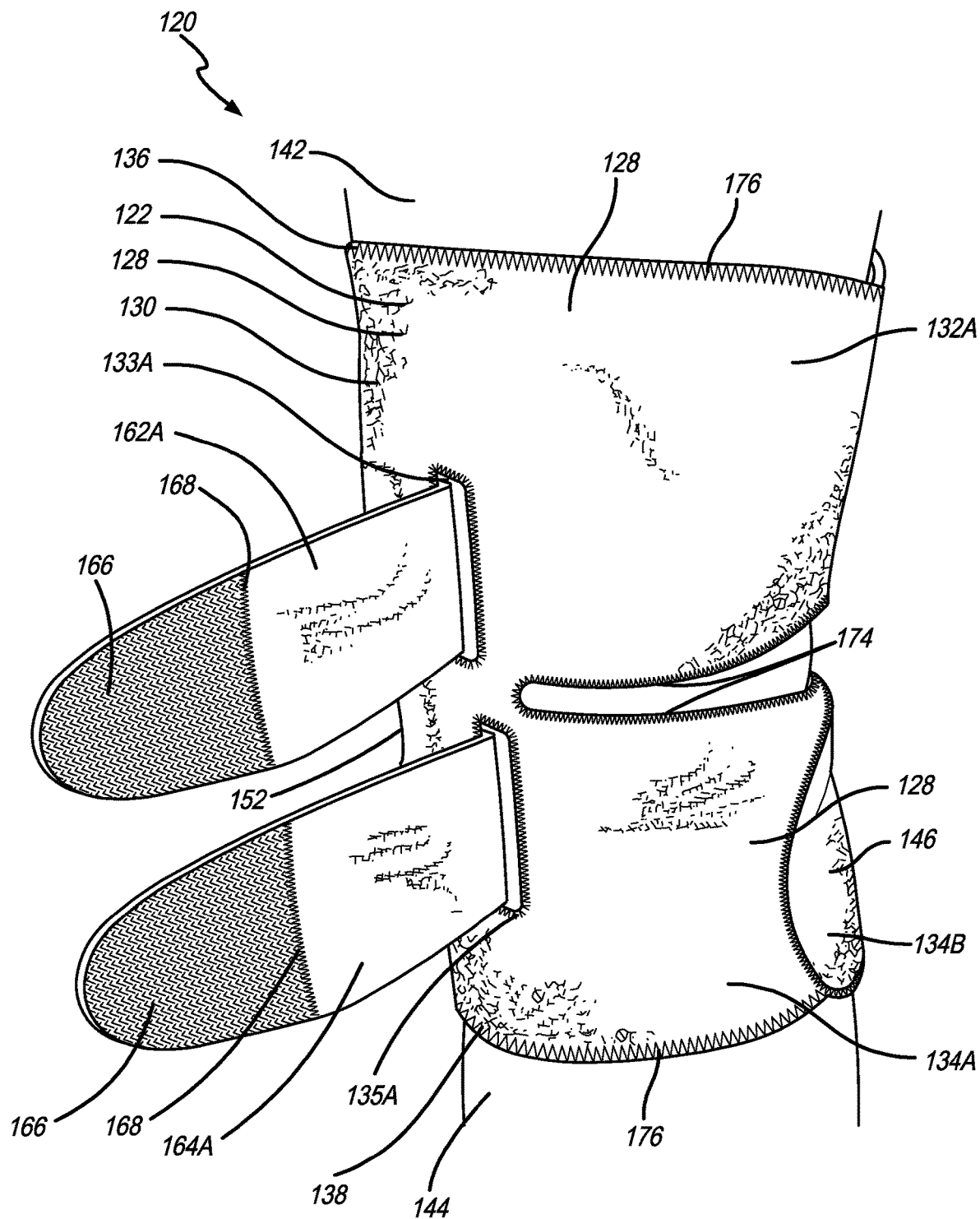
FIG. 4A is a side view of the knee brace of FIGS. 2A-2B, applied to the leg of a person with the base mounting straps fastened, but with the spider straps unfastened.
Figure 4B:
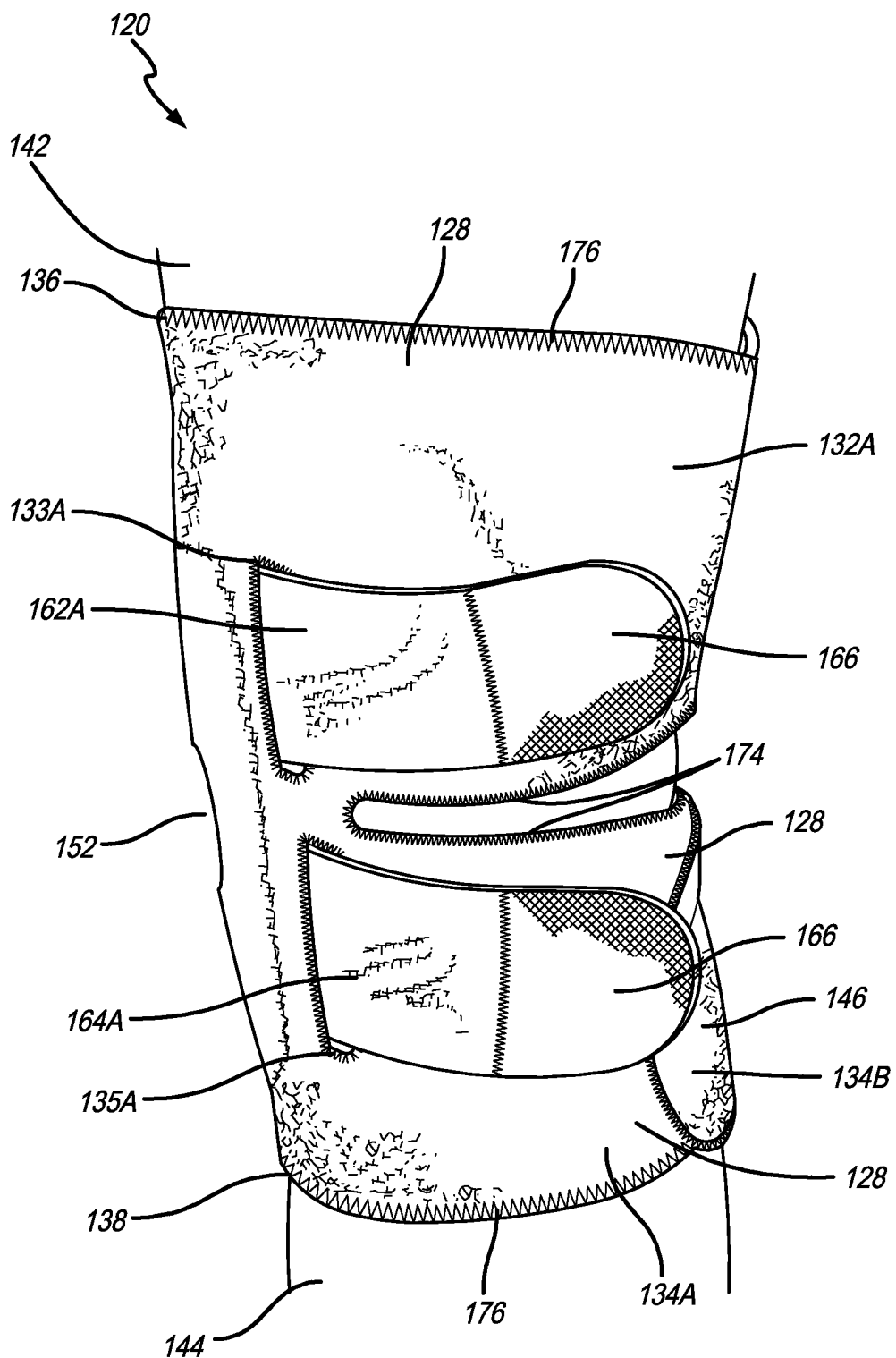
FIG. 4B is a side view of the knee brace of FIGS. 2A-2B, applied to the leg of a person with the base mounting straps fastened, and with the spider straps fastened as well

As best shown in FIGS. 4A and 4B, when the base 122 of the knee brace 120 is applied to the leg of a person, the first upper mounting strap 132A overlaps the second upper mounting strap 132B at the rear of the leg, allowing the hook-type fastening tab 146 at the end of the first upper mounting strap 132A to adhere to the fabric bearing fiber loops 128 on the exterior surface of the second upper mounting strap 132B in order to fasten the knee brace 120 about the upper leg 142 of the wearer. Similarly, the first lower mounting strap 134A overlaps and adheres to the second lower mounting strap 134B at the rear of the leg in order to fasten the knee brace 120 about the lower leg 144 of the wearer.

The base 122 also preferably has a kneecap opening 152 to receive the patella (kneecap) when the brace is worn. The kneecap opening 152 can match the size of the kneecap, so that the kneecap of the wearer extends from the kneecap opening 152 when the brace 120 is worn, although this is not necessary. The kneecap opening 152 is preferably circular in shape, but this is not necessary and other shapes such as a diamond, oval, rectangle, or square shape may be used. In addition to providing direct patella stabilization, the kneecap opening 152 may help to locate the brace 120 with respect to the kneecap during application of the brace 120.

The base 122 may be formed to include a recess 174 between the upper mounting straps 132A, 132B and the lower mounting straps 134A, 134B, so that when the knee brace 120 is fitted upon the leg the gaps on each side form an opening at the rear of the knee, although this is not required. The recess 174 can help to avoid chafing, it can provide ventilation, and it can help avoid bunching or undue restriction of movement.

The base 122 is preferably formed, as shown in FIGS. 2A-2B, as a reclosable sleeve made from a sheet of elastic material that provides generalized support and compression to the knee area, along with therapeutic warming, but other materials may be used. The base 122 may also be formed, for example, as a tubular elastic sleeve shaped to fit snugly about the knee and adjacent leg portions. The base preferably includes edge binding 176, although none of these features are required.

As perhaps best shown in FIG. 2B which shows the interior surface 139 of the base 122, the knee brace 120 includes a spider member 124. The spider member 124 has a spider member central portion 154 extending vertically from an upper edge 156 to a lower edge 158, and has a mid-line axis 160 running vertically down the middle of the spider member central portion 154. The central portion 154 of the spider member 124 is permanently attached to the interior surface 139 of the base 122 by stitches 171 that extend along the mid-line axis 160 of the spider member central portion 54.

The spider member 124 includes a first upper tensioning strap 162A, a second upper tensioning strap 162B, a first lower tensioning strap 164A, and a second lower tensioning strap 164B extending from the central portion 154. Each of the tensioning straps 162A, 162B, 164A, 164B terminates in hook-type fastening tabs 166 suitable for detachable attachment to the fabric bearing fiber loops 128 on the exterior surface of the base 122 and sewn to the tensioning straps with stitches 168. The spider member 124 also has a kneecap opening 170 to receive the kneecap when the brace is worn.

While there are some similarities between the prior art knee brace 20 and a knee brace 120 according to the present invention, there are (without limitation) at least three important differences. First, the spider member 24 of the prior art knee brace 20 is fastened to the exterior surface 31 of the base 22. In contrast, the spider member 124 of the knee brace 120 according to the present invention is fastened to the interior surface 139 of the base 122.

Second, the spider member 24 of the prior art knee brace 20 is fastened to the base 22 by stitches 72 that extend around the periphery of the spider member central portion 54. In contrast, the spider member 124 of the knee brace 120 is fastened to the base 122 by stitches 171 that extend along the mid-line axis 160 of the spider member central portion 154.

Third, both the central portion 54 and the tensioning straps 62A, 62B, 64A, 64B of the spider member 24 of the prior art knee brace 20 are on the exterior surface 31 of the base 22 during normal use. In contrast, in the knee brace 120 the central portion 154 of the spider member 124 is on the interior surface 139 of the base 122, and the tensioning straps 162A, 162B, 164A, and 164B extend through apertures 133A, 133B, 135A, 135B to reach the exterior surface 131 of the base 122.

Figure 5A:
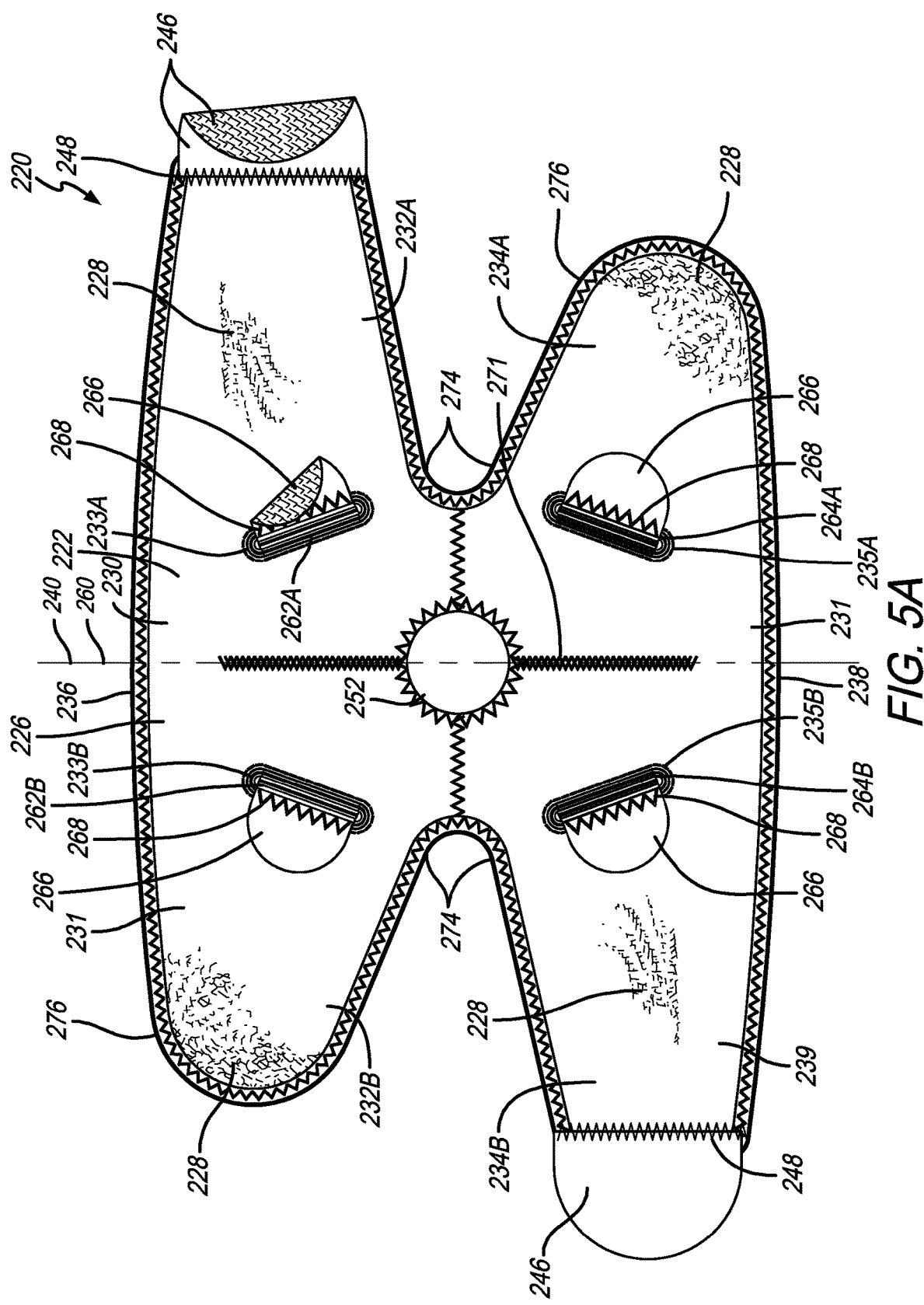
FIG. 5A is a plan view of a second embodiment of a knee brace according to the present invention, having a shaped tensioning member formed of a synthetic fiber that is relatively elastic in all directions and permanently fastened to the interior surface of the base, with the brace laid flat to expose the exterior surface of the brace.
Figure 5B:
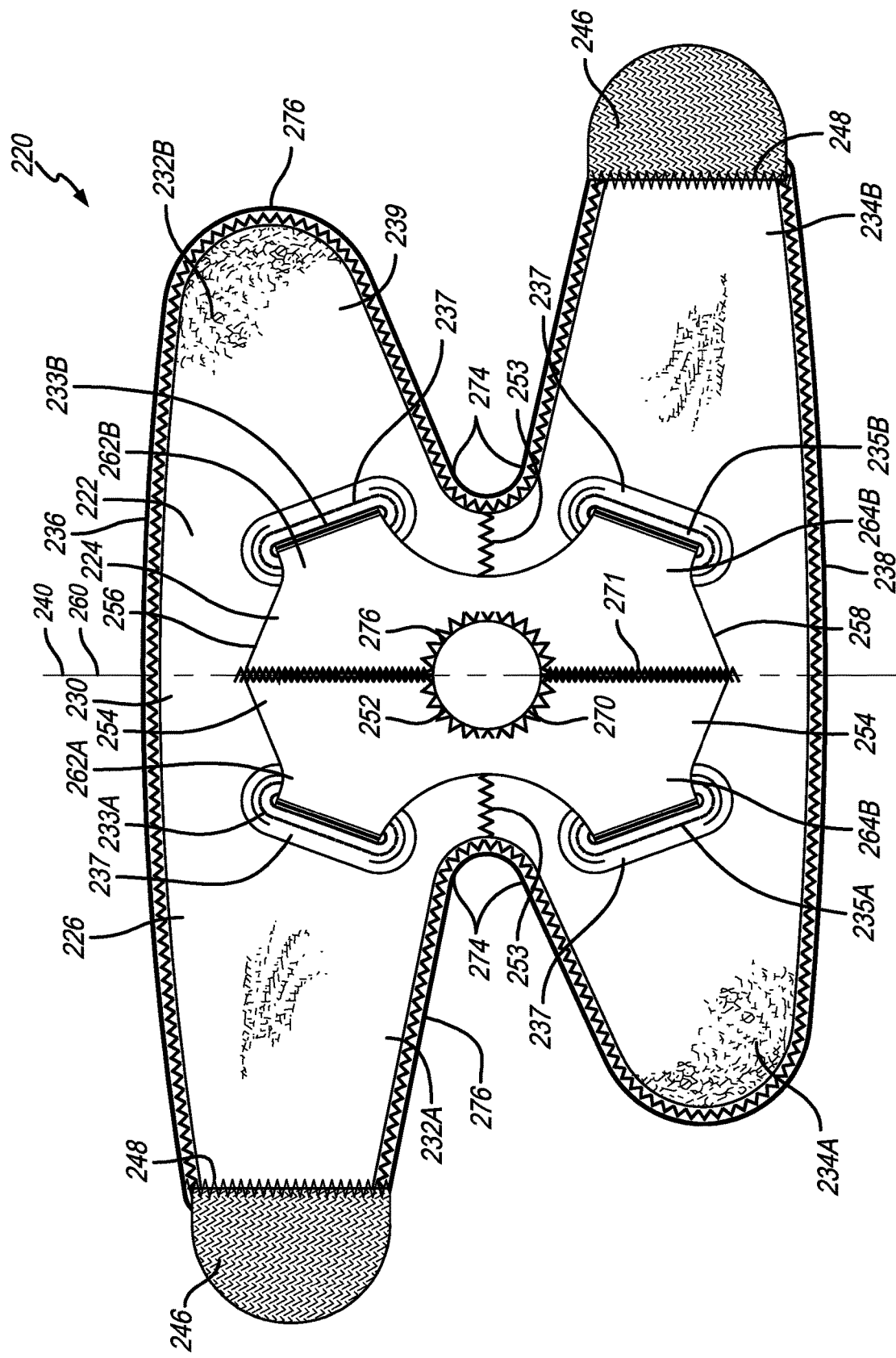
FIG. 5B is a plan view of the knee brace of FIG. 5A, laid flat to expose the interior surface of the brace.
Figure 5C:
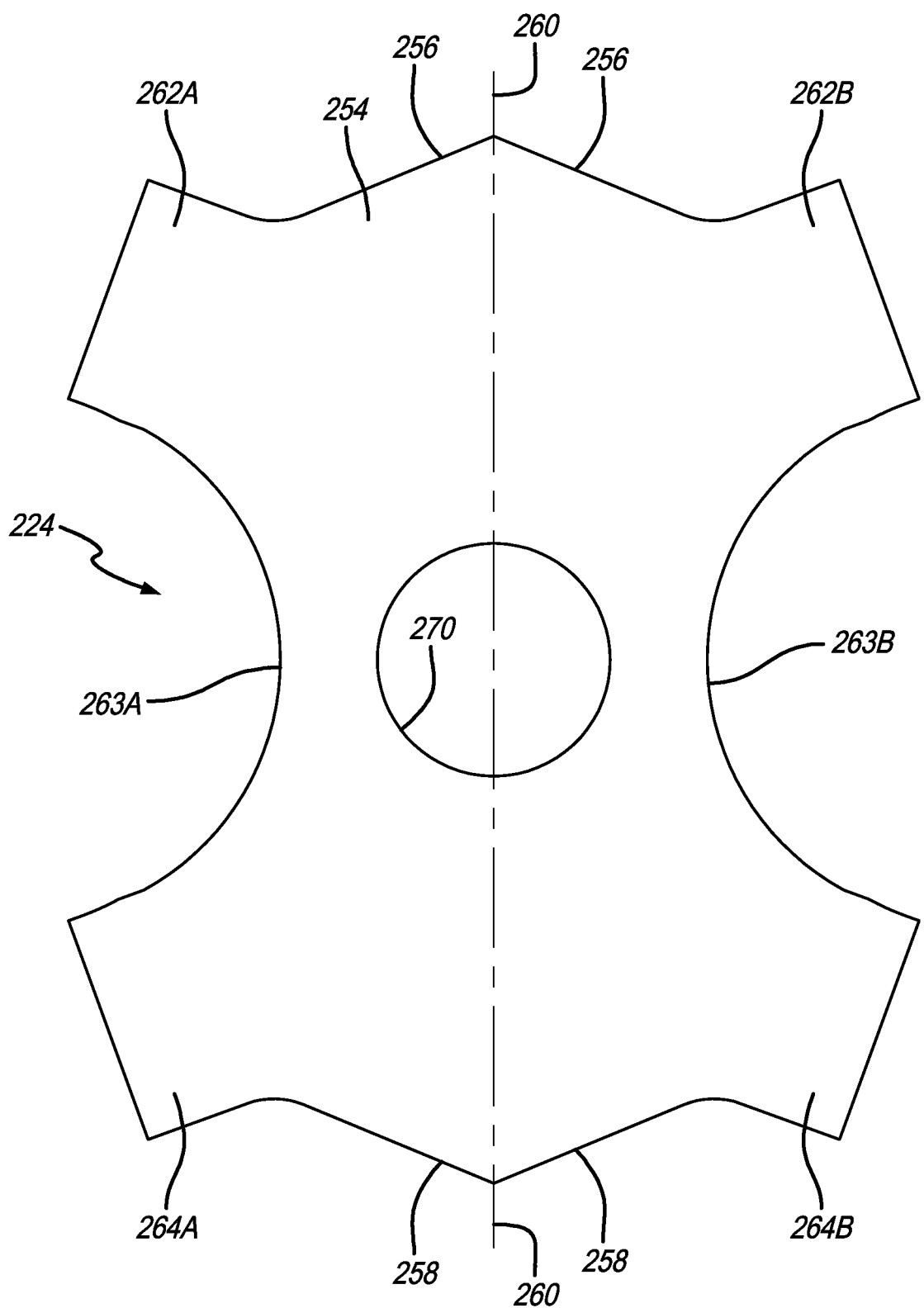
FIG. 5C is a plan view of a shaped tensioning member for use in the knee brace of FIGS. 5A-5B.
Figure 5D:
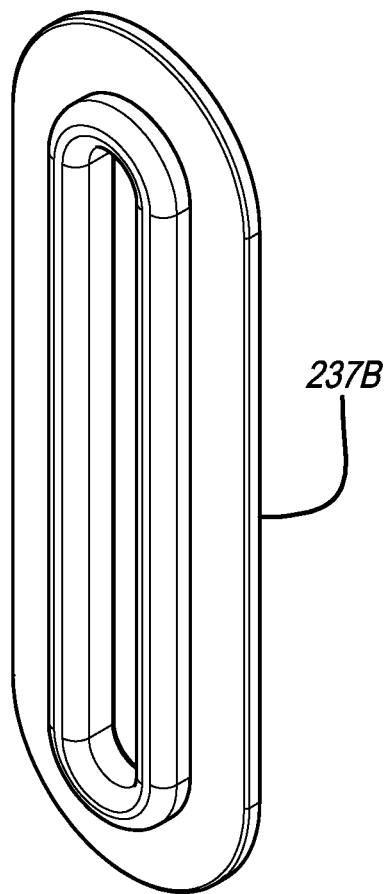
FIGS. 5D-5E are perspective views of an aperture reinforcement base and backing, respectively, for use in the knee brace of FIGS. 5A-5B.
Figure 5E:
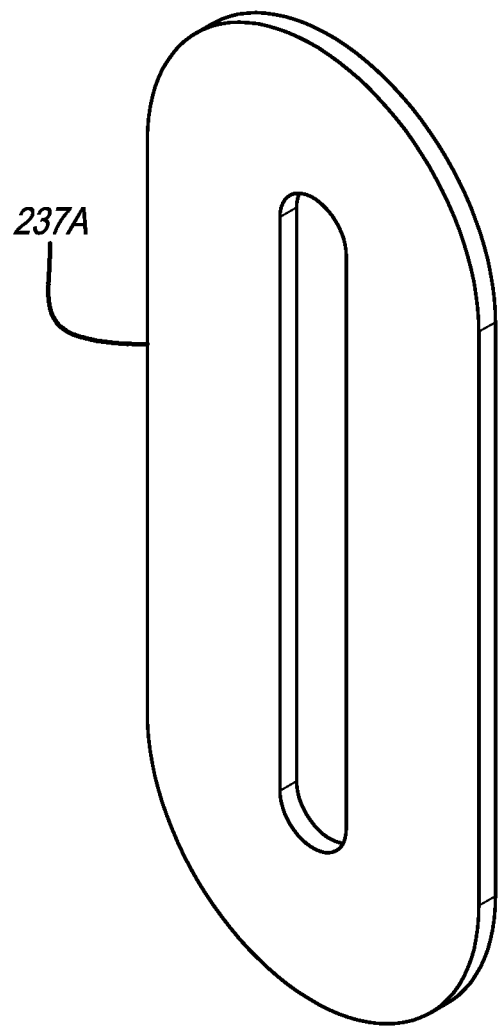

FIGS. 5A-5B are plan views of a second embodiment of a knee brace according to the present invention 220, with the brace laid flat to expose the exterior and interior surfaces of the brace. The knee brace 220 has a shaped tensioning member 224 (shown in isolation in FIG. 5C) permanently fastened to the interior surface of the base. The knee brace 220 also includes reinforced apertures 237 formed with an aperture reinforcement base 237A and aperture reinforcement backing 237B (shown in isolation in FIGS. 5D-5E).

The knee brace 220 includes a base member 222 and a shaped tensioning member 224, each made by cutting planar sheets 226 of one or more elastomeric materials into the desired shapes. The outer surface of the base member 222 is preferably covered with fabric bearing fiber loops 228 that adheres to hook-type material when the fiber loops and hook-type material are pressed together. The shaped tensioning member 224 is preferably formed of a synthetic fiber that is relatively elastic in all directions for example of the type known as spandex in the United States or elasthane, or sold under the trademark LYCRA®, although this is not required and other materials could be used.

The base 222 of the knee brace 220 has a base central portion 230 extending vertically from an upper edge 236 to a lower edge 238, and has a mid-line axis 240 running vertically down the middle of base central portion 230. The base 222 includes a first upper mounting strap 232A, a second upper mounting strap 232B, a first lower mounting strap 234A, and a base second lower mounting strap 234B extending from the central portion 230. The base 222 also includes first upper aperture 233A, second upper aperture 233B, first lower aperture 235A, and second lower aperture 235B, all formed as reinforced apertures 237 in the base 222.

As perhaps best shown in FIG. 5B which shows the interior surface 239 of the base 222, the first upper mounting strap 232A and first lower mounting strap 234A terminate in hook-type strap fastening tabs 246 suitable for detachable attachment to the fabric bearing fiber loops 228 on the external surface 231 of the base 222. The hook-type strap fastening tabs 246 are sewn to the mounting straps with stitches 248.

The knee brace 220 is applied and fastened to the leg of a person in a similar fashion as the knee brace 120 shown in FIGS. 3A-3B and 4A-4B. The base 222 also preferably has a kneecap opening 252 to receive the patella (kneecap) when the brace is worn, and may be formed to include a side recess 274 between the upper mounting straps 232A, 232B and the lower mounting straps 234A, 234B. The base preferably includes edge binding 276, although none of these features are required.

As perhaps best shown in FIG. 5B which shows the interior surface 239 of the base 222, the knee brace 220 includes a shaped tensioning member 224. As perhaps best shown in FIG. 5C, the shaped tensioning member 224 has a central portion 254, an upper edge 256, a lower edge 258, a first lateral side 263A, a second lateral side 263B, and a central portion mid-line axis 260. The shaped tensioning member 224 also includes a first upper tensioning strap 262A, a second upper tensioning strap 262B, a first lower tensioning strap 264A, and a second lower tensioning strap 264B. The shaped tensioning member 224 terminates in hook-type fastening tabs 266 suitable for detachable attachment to the fabric bearing fiber loops 228 on the exterior surface of the base 222 and sewn to the tensioning straps with stitches 268. The shaped tensioning member 224 may include a kneecap opening 270, and may be permanently attached to the base 222 by mid-line stitches 271 that extend along the mid-line axis 260 of the central portion 254.

Figure 6A:
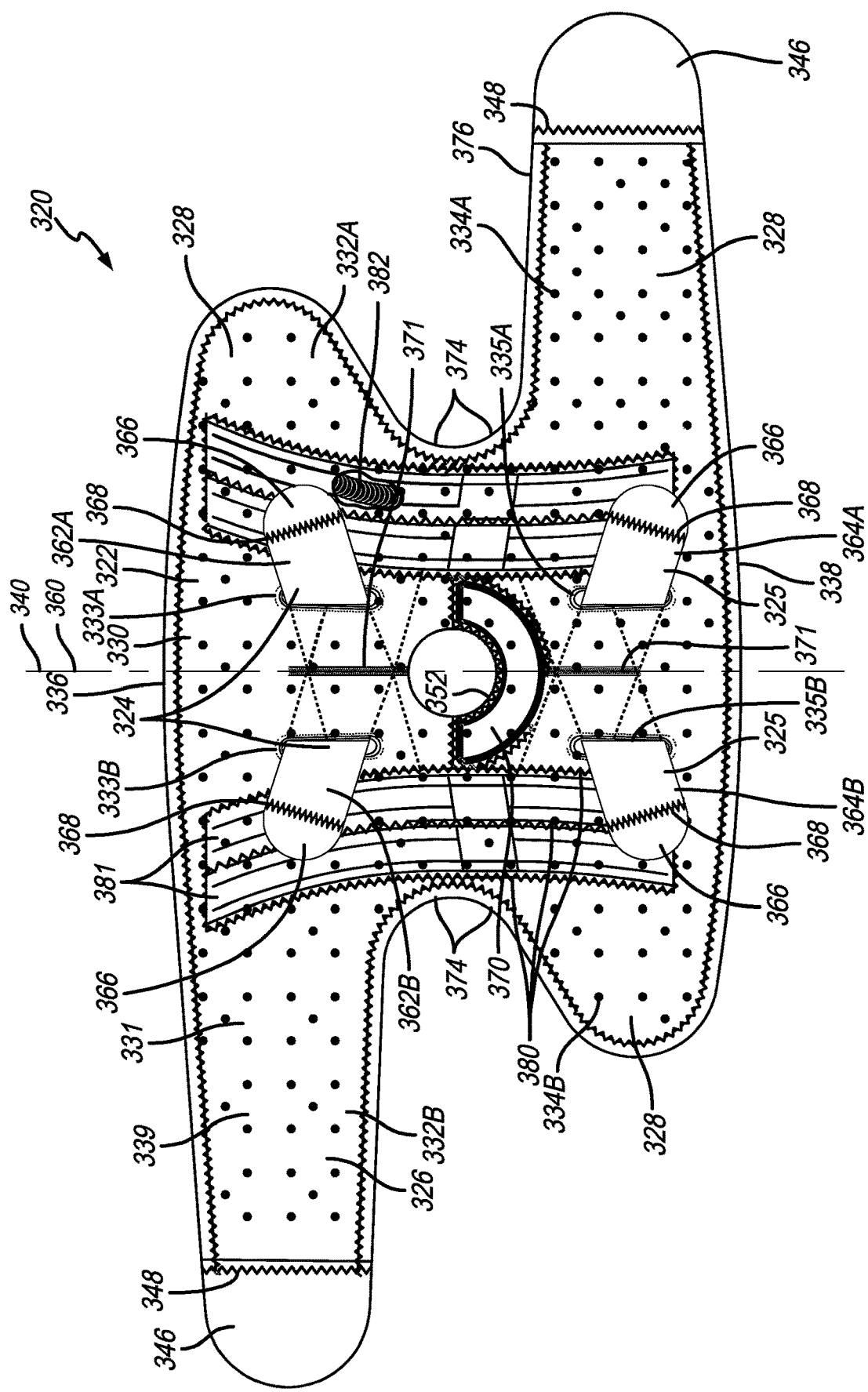
FIG. 6A is a plan view of a third embodiment of a knee brace according to the present invention, having upper and lower crossed straps along with resilient stays, with the brace laid flat to expose the exterior surface of the brace.
Figure 6B:
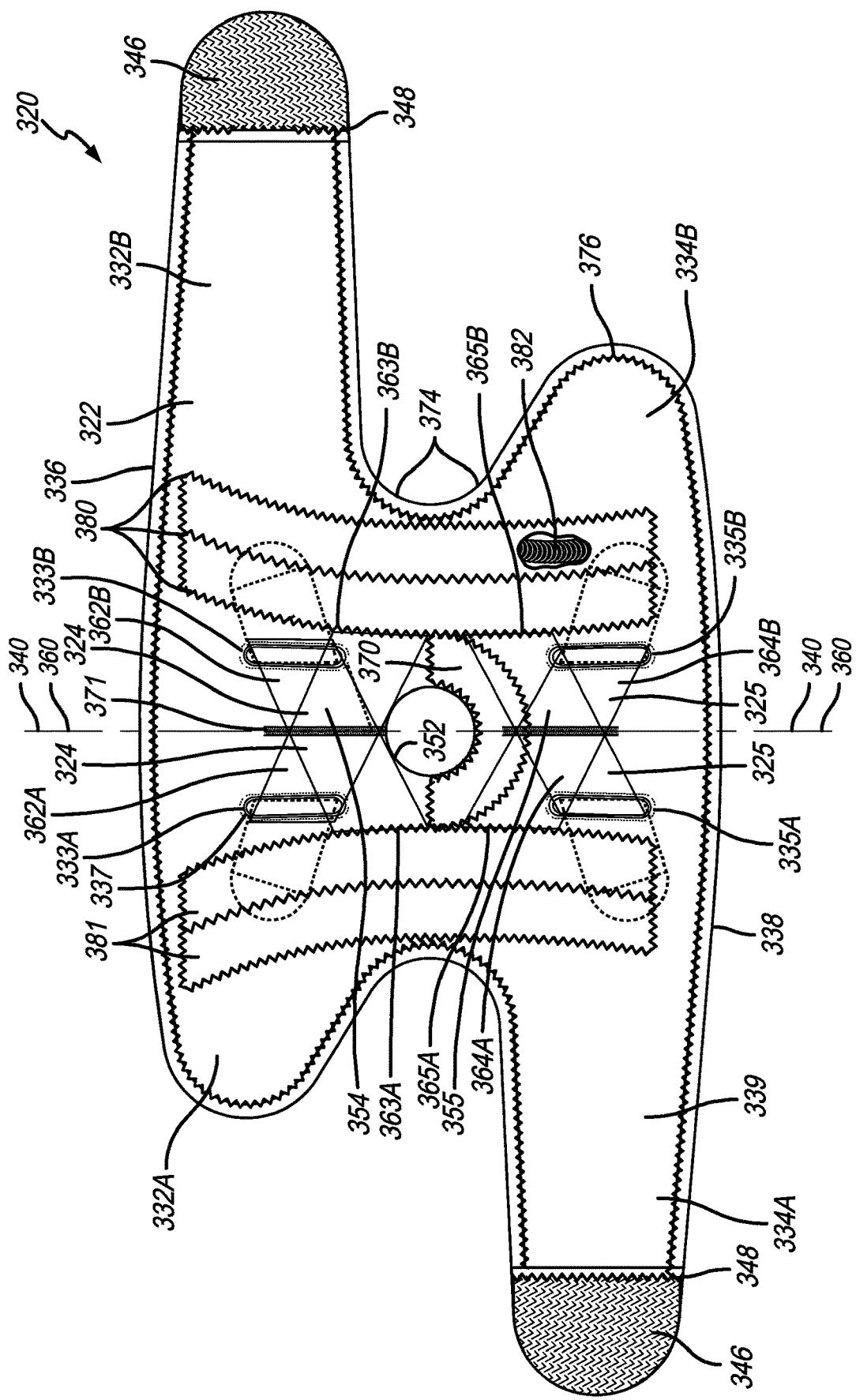
FIG. 6B is a plan view of the knee brace of FIG. 6A, laid flat to expose the interior surface of the brace.

FIGS. 6A-6B are plan views of a third embodiment of a knee brace according to the present invention 320, with the brace laid flat to expose the exterior and interior surfaces of the brace. The knee brace 320 has resilient stays and features upper and lower crossed elastic straps permanently fastened to the interior surface of the base. The knee brace 320 also includes reinforced apertures 337.

The knee brace 320 includes a base member 322 made by cutting planar sheets 326 of one or more elastomeric materials into the desired shape. The exterior surface 331 of the base member 322 is preferably covered with fabric bearing fiber loops 328 that adheres to hook-type material when the fiber loops and hook-type material are pressed together. The knee brace 320 also includes upper crossed straps 324 and lower crossed straps 325, preferably formed of a material that is elastic along the length of the straps.

The base 322 of the knee brace 320 has a base central portion 330 extending vertically from an upper edge 336 to a lower edge 338, and has a mid-line axis 340 running vertically down the middle of base central portion 330. The base 322 includes a first upper mounting strap 332A, a second upper mounting strap 332B, a first lower mounting strap 334A, and a base second lower mounting strap 334B extending from the central portion 330. The base 322 also includes first upper aperture 333A, second upper aperture 333B, first lower aperture 335A, and second lower aperture 335B, all formed as reinforced apertures 337 in the base 322.

As perhaps best shown in FIG. 2B which shows the interior surface 339 of the base 322, the first upper mounting strap 332A and first lower mounting strap 334A terminate in hook-type strap fastening tabs 346 suitable for detachable attachment to the fabric bearing fiber loops 328 on the external surface 331 of the base 322. The hook-type strap fastening tabs 346 are sewn to the mounting straps with stitches 348.

The knee brace 320 is applied and fastened to the leg of a person in a similar fashion as the knee brace 120 shown in FIGS. 3A-3B and 4A-4B. The base 322 also preferably has a kneecap opening 352 to receive the patella (kneecap) when the brace is worn, and may be formed to include a recess 374 between the upper mounting straps 332A, 332B and the lower mounting straps 334A, 334B. The base preferably includes edge binding 376, although none of these features are required.

As perhaps best shown in FIG. 6B which shows the interior surface 339 of the base 322, the knee brace 320 includes upper crossed straps 324 with a central portion 354 and lower crossed straps 325 with a central portion 355. The crossed straps have a mid-line axis 360. The upper crossed straps 324 comprise first upper crossed tensioning strap 362A and second upper crossed tensioning strap 362B. The lower crossed straps 325 comprise first lower crossed tensioning strap 364A and second lower crossed tensioning strap 364B. The tensioning straps terminate in hook-type Velcro fastening tabs 366 suitable for detachable attachment to the fabric bearing fiber loops 328 on the exterior surface of the base 322 and sewn to the tensioning straps with stitches 368. The base 322 may include a patella buttress 370. The upper crossed straps 324 and lower crossed straps 325 may be permanently attached to the base 322 by stitches 371 that extend along the mid-line axis 360 and by stiches 363A, 363B, 365A, 365B at the fixed ends of the crossed straps.

The base 320 may include additional lateral support, for example one or more resilient stays 382 (shown in FIG. 7E) placed in pockets 381 formed using an additional sheet material secured to the base by resilient stay channel stitching 380.

Figure 7A:
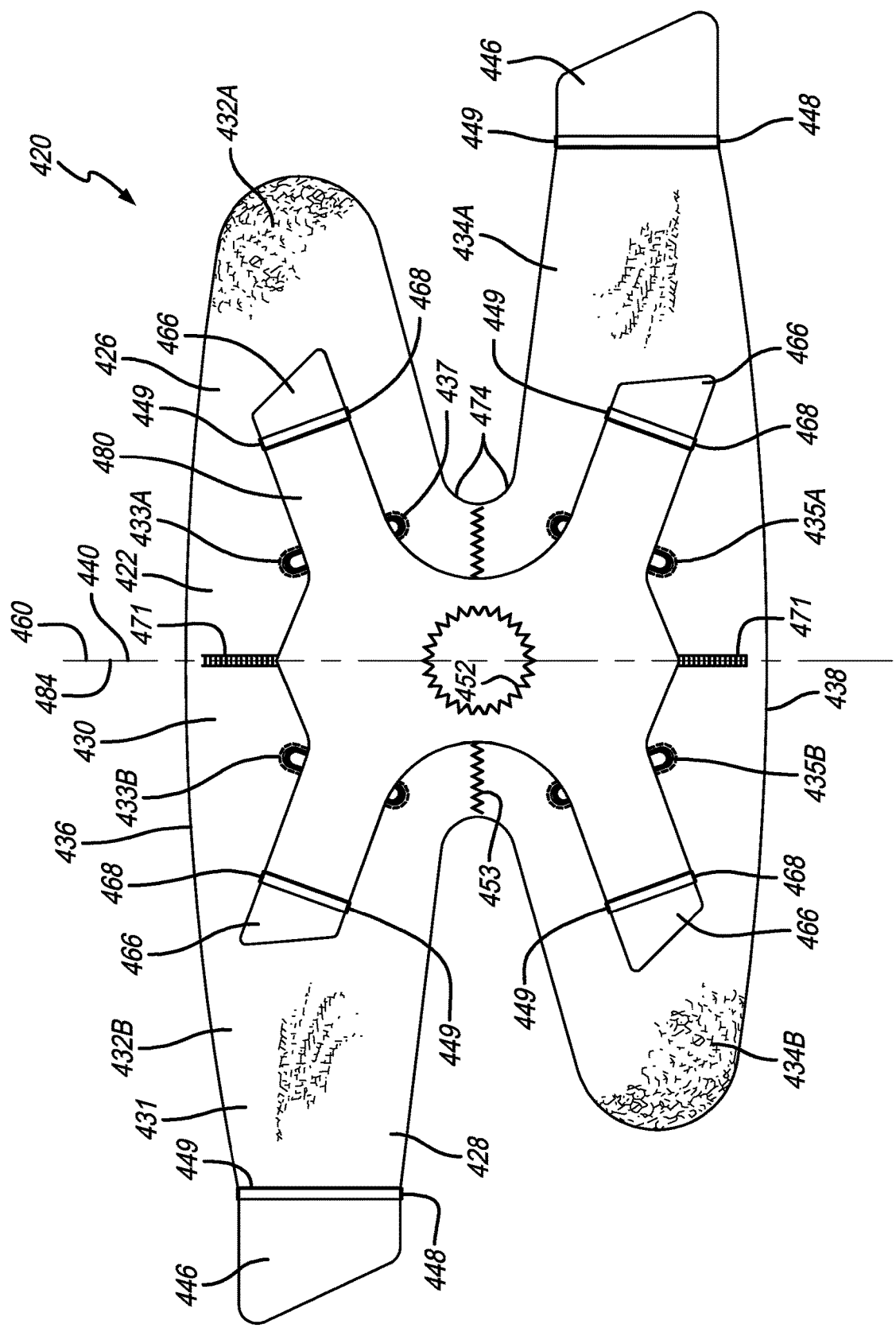
FIG. 7A is a plan view of a fourth embodiment of a knee brace according to the present invention, having an external mesh layer and an internal shaped tensioning member having both elastic and inelastic components, with the brace laid flat to expose the exterior surface of the brace.
Figure 7C:
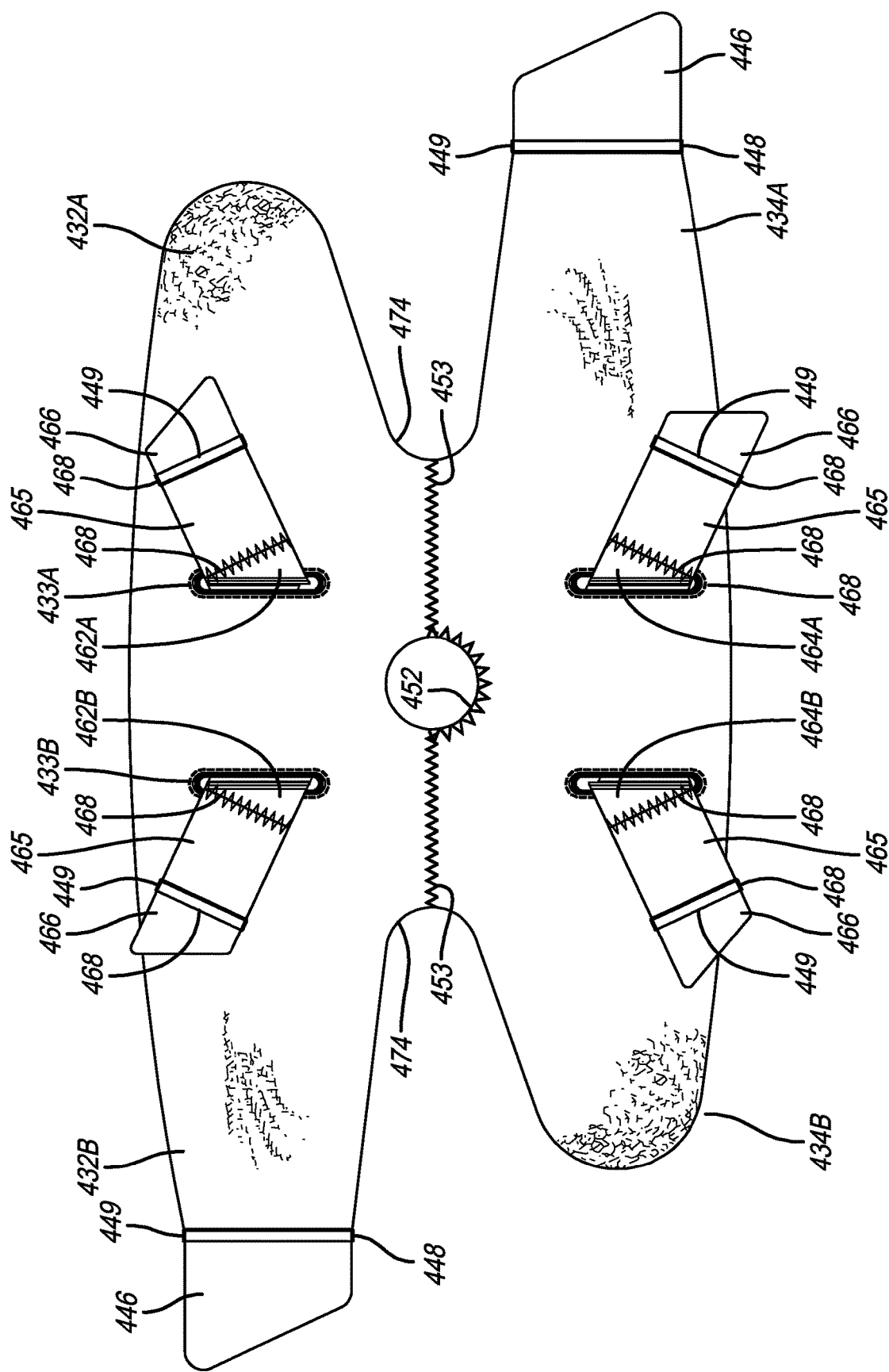
FIG. 7C is a plan view of the knee brace of FIG. 7A, laid flat to expose the exterior surface of the brace and with the external mesh layer removed to reveal the construction of the internal shaped tensioning member that may have both elastic and inelastic components.

FIGS. 7A-7B are plan views of a fourth embodiment of a knee brace according to the present invention 420, with the brace laid flat to expose the exterior and interior surfaces of the brace. Similar to knee brace 220 of FIGS. 5A-5B, the knee brace 420 has a shaped tensioning member 424 (shown in isolation in FIG. 7C) formed of a synthetic fiber that is relatively elastic in all directions and permanently fastened to the interior surface of the base. The knee brace 420 also includes reinforced apertures 437 and an external mesh layer 480 (shown in isolation in FIG. 7D).

The knee brace 420 includes a base member 422 and a shaped tensioning member 424, each made by cutting planar sheets 426 of one or more elastomeric materials into the desired shapes. The outer surface of the base member 422 is preferably covered with fabric bearing fiber loops 428 that adheres to hook-type material when the fiber loops and hook-type material are pressed together. The shaped tensioning member 424 is preferably formed of a synthetic fiber that is relatively elastic in all directions for example of the type known as spandex in the United States or elasthane, or sold under the trademark LYCRA®, although this is not required and other materials could be used.

The base 422 of the knee brace 420 has a base central portion 430 extending vertically from an upper edge 436 to a lower edge 438, and has a mid-line axis 440 running vertically down the middle of base central portion 430. The base 422 includes a first upper mounting strap 432A, a second upper mounting strap 432B, a first lower mounting strap 434A, and a base second lower mounting strap 434B extending from the central portion 430. The base 422 also includes first upper aperture 433A, second upper aperture 433B, first lower aperture 435A, and second lower aperture 435B, all formed as reinforced apertures 437 in the base 422.

As perhaps best shown in FIG. 7B which shows the interior surface 439 of the base 422, the first upper mounting strap 432A and first lower mounting strap 434A terminate in hook-type strap fastening tabs 446 suitable for detachable attachment to the fabric bearing fiber loops 428 on the external surface 431 of the base 422. The hook-type strap fastening tabs 446 are sewn to the mounting straps with stitches 448, and may include one or more flair devices 449, such as reflectors, lights, glow-in-the-dark materials, or bright colors.

The knee brace 420 is applied and fastened to the leg of a person in a similar fashion as the knee brace 120 shown in FIGS. 3A-3B and 4A-4B. The base 422 also preferably has a kneecap opening 452 to receive the patella (kneecap) when the brace is worn. The base 422 may be formed to include a recess 474 between the upper mounting straps 432A, 432B and the lower mounting straps 434A, 434B. The base 422 can be formed using multiple sheets, or with a simple cut with stitching 453 to contour the base to fit the leg more closely.

As perhaps best shown in FIG. 7B which shows the interior surface 439 of the base 422, the knee brace 420 includes a shaped tensioning member 424 with a central portion 454, an upper edge 456, a lower edge 458, a first lateral side 463A, a second lateral side 463B, and a central portion mid-line axis 460. The shaped tensioning member 424 also includes a first upper tensioning strap 462A, a second upper tensioning strap 462B, a first lower tensioning strap 464A, and a second lower tensioning strap 464B. As perhaps best shown in FIG. 7C, the tensioning straps may include one or more inelastic portions 465.

The shaped tensioning member 424 terminates in hook-type fastening tabs 466 suitable for detachable attachment to the fabric bearing fiber loops 428 on the exterior surface of the base 422 and sewn to the tensioning straps with stitches 468. The shaped tensioning member 424 may include a kneecap opening 470, and may be permanently attached to the base 422 by mid-line stitches 471.

Figure 7D:
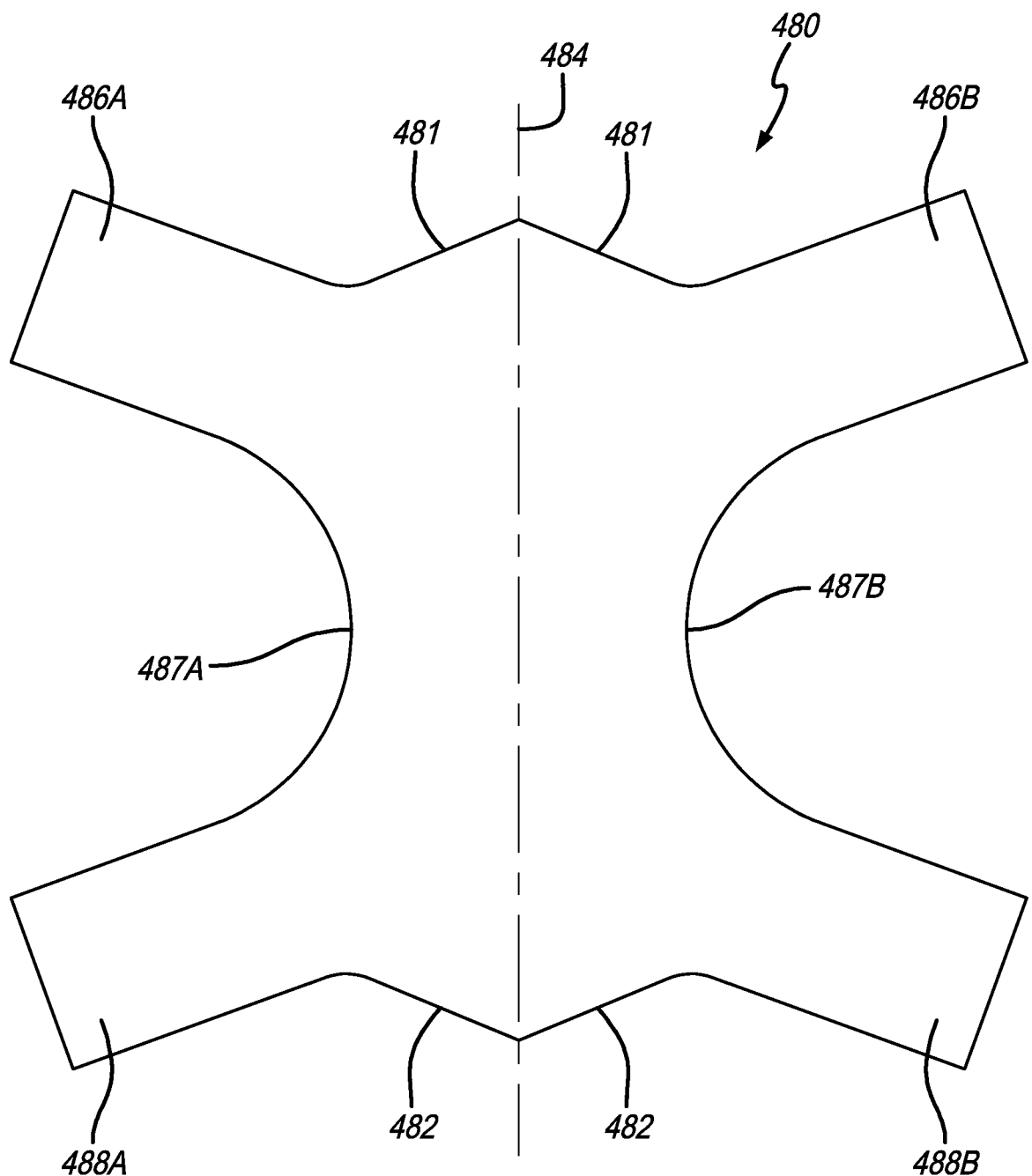
FIG. 7D is a plan view of an external mesh layer for use in the knee braces of FIGS. 7A-7C.
Figure 7E:
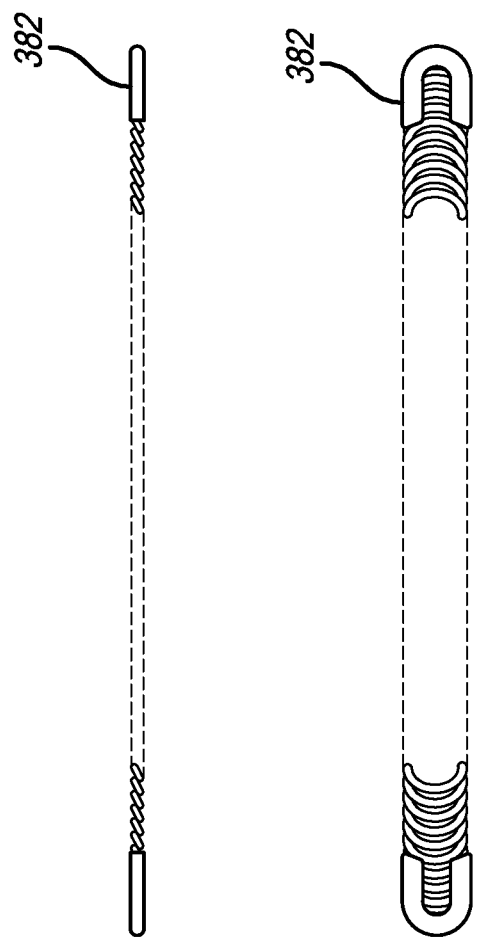
FIG. 7E shows a resilient stay member for use in the knee brace of FIGS. 6A-6B, 7A-7C, and 8A-8C.

As perhaps best shown in FIG. 7A, the knee brace 420 includes an external mesh layer 480. As shown in FIG. 7D, the external mesh layer 480 has an upper edge 481, a lower edge 482, a mid-line axis 484, an first upper arm 486A, a second upper arm 486B, a first lateral side 487A, a second lateral side 487B, a first lower arm 488A, and a second lower arm 488B. The exterior mesh layer 480 is permanently fastened to the first upper tensioning strap near the first strap end, to the second upper tensioning strap near the second strap end, to the first lower tensioning strap near the third strap end, and to the second lower tensioning strap near the fourth strap end. The exterior mesh layer 480 may be otherwise unattached to the base 422.

Figure 8A:
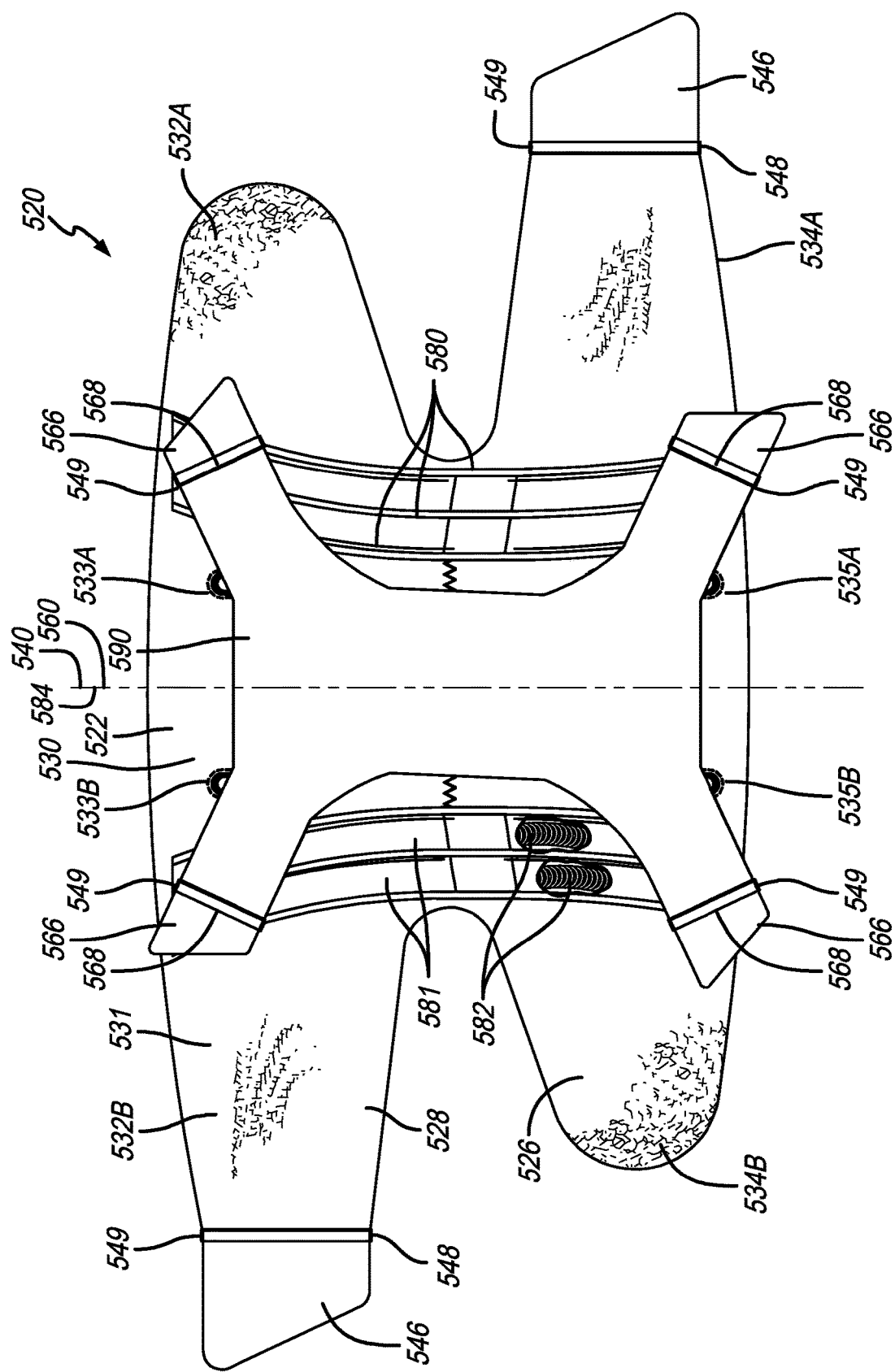
FIG. 8A is a plan view of a fifth embodiment of a knee brace according to the present invention, having an external mesh layer and upper and lower crossed straps that may have both elastic and inelastic portions, with the brace laid flat to expose the exterior surface of the brace.
Figure 8B:
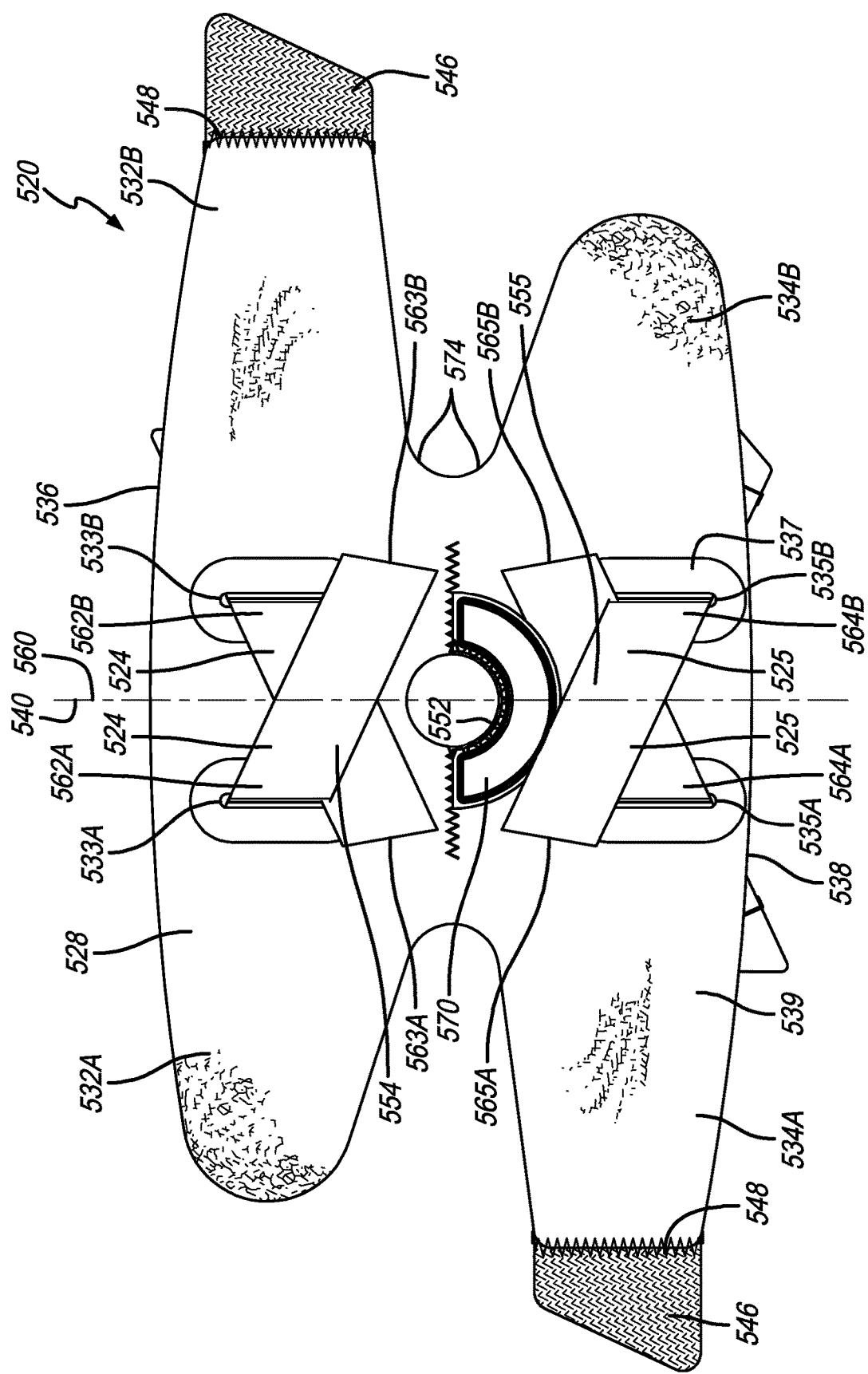
FIG. 8B is a plan view of the knee brace of FIG. 8A, laid flat to expose the interior surface of the brace.
Figure 8C:
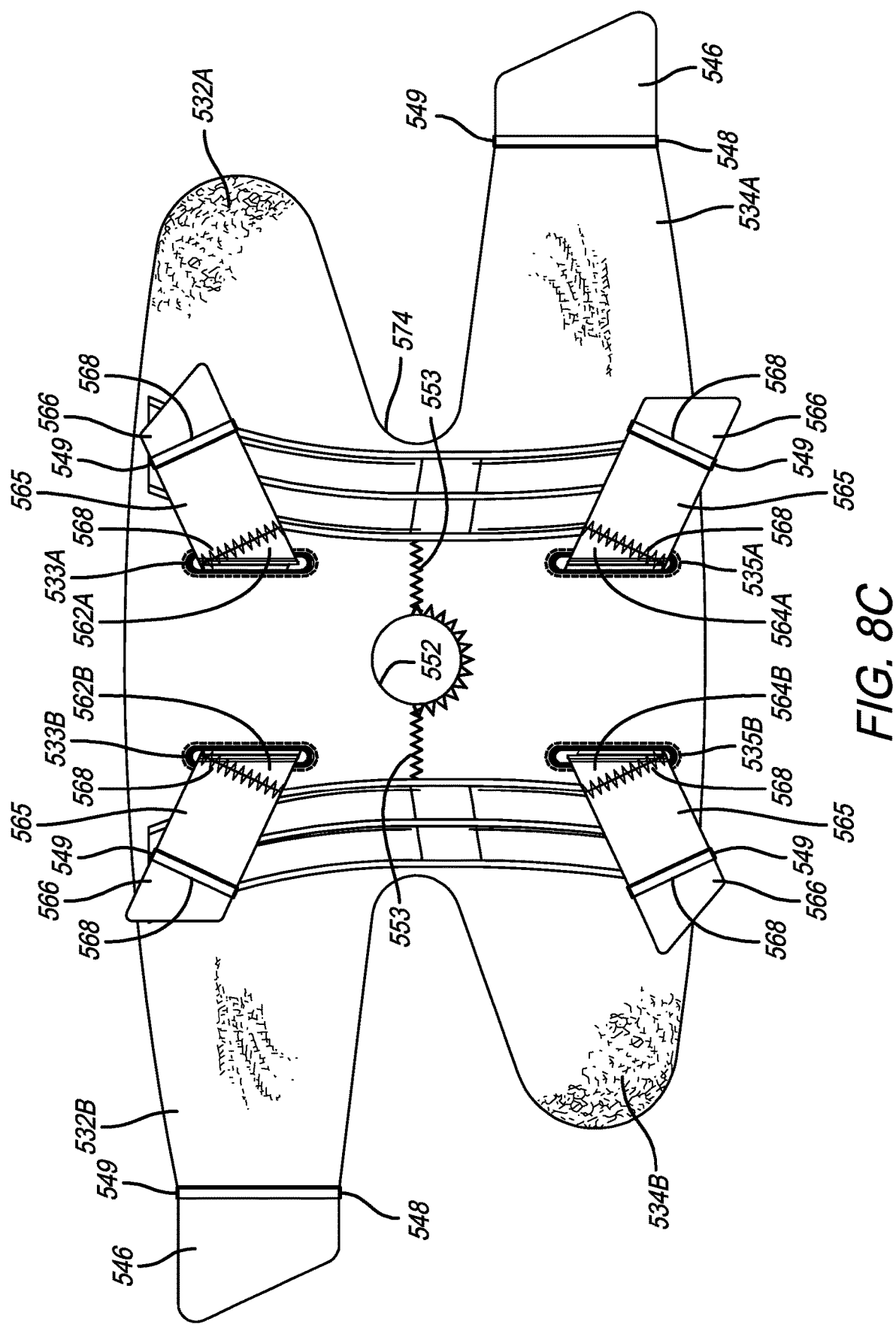
FIG. 8C is a plan view of the knee brace of FIG. 8A, laid flat to expose the exterior surface of the brace and with the external mesh layer removed to reveal the construction of the upper and lower crossed straps that may have both elastic and inelastic portions.

FIGS. 8A-8B are plan views of a fifth embodiment of a knee brace according to the present invention 520, with the brace laid flat to expose the exterior and interior surfaces of the brace. Similar to knee brace 320 of FIGS. 6A-6B, the knee brace 520 has upper and lower crossed elastic straps permanently fastened to the interior surface of the base. The knee brace 520 also includes reinforced apertures 537 and resilient stays 582, and features an external mesh layer 590 (shown in isolation in FIG. 8D).

The knee brace 520 includes a base member 522 made by cutting planar sheets 526 of one or more elastomeric materials into the desired shape. The outer surface of the base member 522 is preferably covered with fabric bearing fiber loops 528 that adheres to hook-type material when the fiber loops and hook-type material are pressed together. The knee brace 520 also includes upper crossed straps 524 and lower crossed straps 525, preferably formed of a material that is elastic along the length of the straps.

The base 522 of the knee brace 520 has a base central portion 530 extending vertically from an upper edge 536 to a lower edge 538, and has a mid-line axis 540 running vertically down the middle of base central portion 530. The base 522 includes a first upper mounting strap 532A, a second upper mounting strap 532B, a first lower mounting strap 534A, and a base second lower mounting strap 534B extending from the central portion 530. The base 522 also includes first upper aperture 533A, second upper aperture 533B, first lower aperture 535A, and second lower aperture 535B, all formed as reinforced apertures 537 in the base 522.

As perhaps best shown in FIG. 8B which shows the interior surface 539 of the base 522, the first upper mounting strap 532A and first lower mounting strap 534A terminate in hook-type strap fastening tabs 546 suitable for detachable attachment to the fabric bearing fiber loops 528 on the external surface 531 of the base 522. The hook-type strap fastening tabs 546 are sewn to the mounting straps with stitches 548.

The knee brace 520 is applied and fastened to the leg of a person in a similar fashion as the knee brace 120 shown in FIGS. 3A-3B and 4A-4B. The base 522 also preferably has a kneecap opening 552 to receive the patella (kneecap) when the brace is worn. The base 522 may be formed to include a recess 574 between the upper mounting straps 532A, 532B and the lower mounting straps 534A, 534B.

As perhaps best shown in FIG. 2B which shows the interior surface 539 of the base 522, the knee brace 520 includes upper crossed straps 524 with a central portion 554 and lower crossed straps 525 with a central portion 555. The crossed straps have a mid-line axis 560. The upper crossed straps 524 comprise first upper crossed tensioning strap 562A and second upper crossed tensioning strap 562B. The lower crossed straps 525 comprise first lower crossed tensioning strap 564A and second lower crossed tensioning strap 564B. The tensioning straps terminate in hook-type Velcro fastening tabs 566 suitable for detachable attachment to the fabric bearing fiber loops 528 on the exterior surface of the base 522 and sewn to the tensioning straps with stitches 568. The base 522 may include a patella buttress 570. The upper crossed straps 524 and lower crossed straps 525 may be permanently attached to the base 522 by mid-line stitches 571 that extend along the mid-line axis 560 and by stitches 563A, 563B, 565A, 565B at the fixed ends of the crossed straps.

The base 520 may include additional lateral support, for example one or more resilient stays 582 placed in pockets 581 formed using an additional sheet material secured to the base by resilient stay channel stitching 580.

Figure 8D:
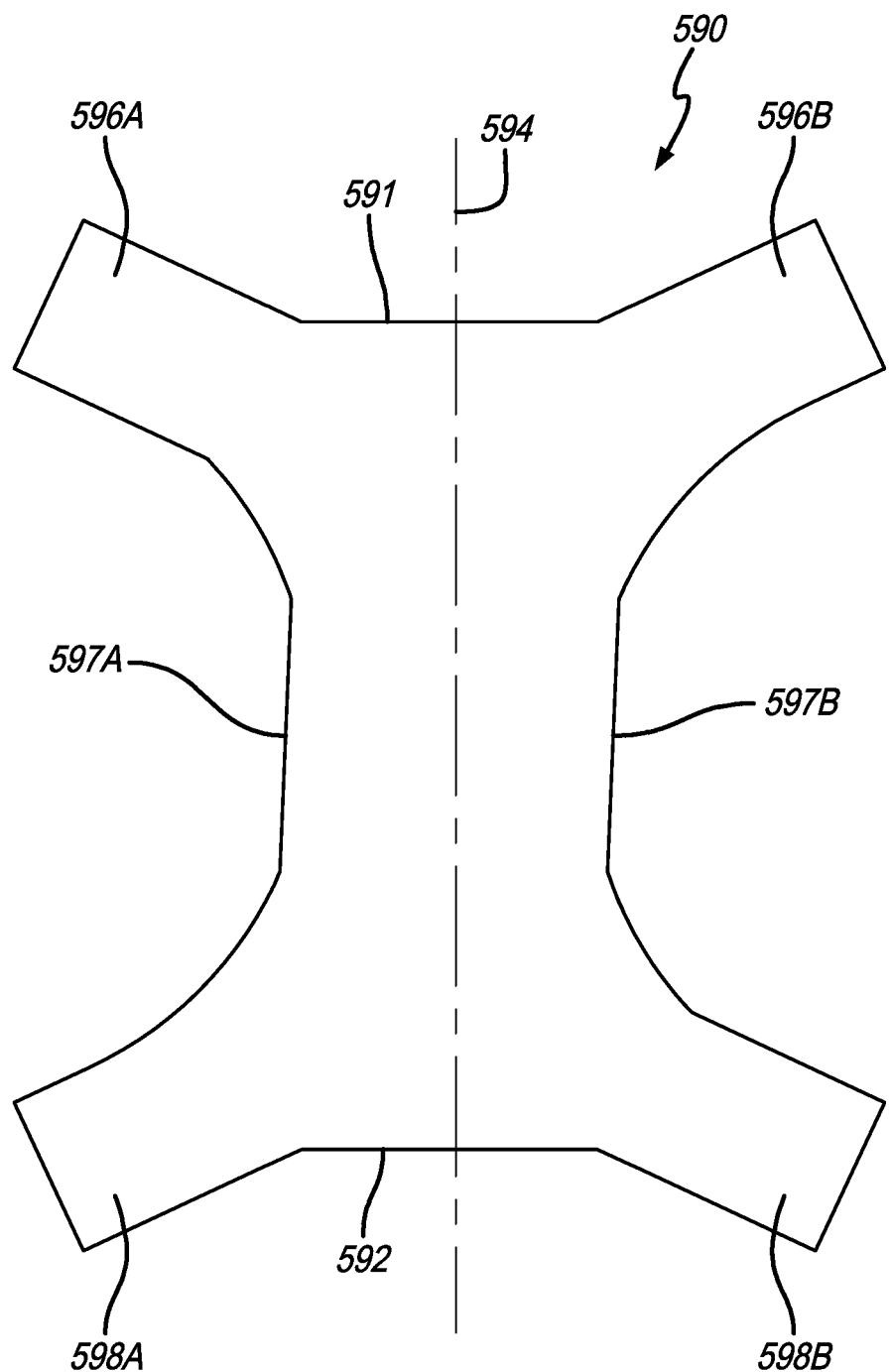
FIG. 8D is a plan view of an external mesh layer for use in the knee brace of FIGS. 8A-8C.

As perhaps best shown in FIG. 8A, the knee brace 520 includes an external mesh layer 590. As shown in FIG. 8D, the external mesh layer 590 has an upper edge 591, a lower edge 592, a mid-line axis 594, an first upper arm 596A, a second upper arm 596B, a first lateral side 597A, a second lateral side 597B, a first lower arm 598A, and a second lower arm 598B. The exterior mesh layer 590 is permanently fastened to the first upper tensioning strap near the first strap end, to the second upper tensioning strap near the second strap end, to the first lower tensioning strap near the third strap end, and to the second lower tensioning strap near the fourth strap end. The exterior mesh layer 590 may be otherwise unattached to the base 522.

There are various possibilities with regard to alternative embodiments of a knee brace according to the invention.

Although in a preferred embodiment the knee brace includes a base which is formed as a reclosable sleeve made from a sheet of elastic material, this is not required. For example, the base may also be formed of a tubular elastic sleeve shaped to fit snugly about the knee and adjacent leg portions. The base does not need to include a kneecap opening, and the kneecap opening, if present, could have a variety of shapes, e.g. circular, square, rectangular, elliptical, diamond, trapezoidal, or any substantial equivalent. All such alternative embodiments will be referred to herein as a base.

Although in a preferred embodiment the lateral sides of the base each terminate in upper and lower fastening straps, with a side recess between the upper and lower fastening straps, this is not required. For example, the sides of the base, or portions thereof, could be straight.

Although in a preferred embodiment the base is detachably fastened about the leg of the wearer using hook and loop material of the type which adheres when pressed together, this is not required. For example, other fasteners such as buttons, clasps, buckles, pins, zippers, straps, buttons or other substantial equivalents may be substituted for the hook and loop type fastener material.

Although in a preferred embodiment, various components are permanently fastened together using stitches, this is not required. For example, other means such as glue, thermal bonding, or other substantial equivalents could be used.

One or more upright support members may be provided on one side, or on both sides, of the base of the knee brace, to provide support and protect the knee against abnormal motions, although this is not required. The upright support members may be formed, for example, by placing a resilient stay member in an elongated side pocket. The resilient stay members may be comprised of a flattened spiral core of stainless steel or other flexible material of conventional construction commonly used in various types of braces.

The elongate side pocket may be formed, for example, between vertical sewn seams that fix a side pocket cover strip to the base. The side pocket cover strip may be made of the same elastic sheet material as the base, although this is not necessary. Edge binding may be fastened to the edges of the side pocket cover strips, although this is not necessary.

The exact number, location, and construction of the upright support members may vary if provided. For example, there may be a single elongated side pocket forming only one upright support member, or there may be one or more elongated side pockets on each side of the knee with a resilient stay in each elongated side pocket. The elongated side pockets may be openable at one end to allow removal of the resilient stays, so that the brace may be washed or so that different resilient stays may be inserted to adjust the amount and type of support provided. The upright support members may include mechanical hinges, plastic rods, metal rods, narrow strips of reinforcing sheet material, or other substantial equivalents, or a combination of these various alternatives.

Advantageously, the external surface of the front of a knee brace according to the invention does not bear any structure, and can be smooth except for any stitches that secure the spider member to the inside of the base. The smooth external surface can be maintained, for example to provide an attractive and clean appearance that will not snag or obstruct motion during use. Alternatively other structures such as thick knee pads for use in contact sports like football or in trades like concrete or floor tile work, or slippery material for use in sports like volleyball, could be positioned on the external surface for particular applications.

It is understood that the invention is not confined to the embodiments set forth herein as illustrative, but embraces all such forms thereof that come within the scope of the following claims.

What is claimed is:
1. A knee brace, comprising:
   (a) a base wearable in snug covering relationship to portions of a knee to extend all the way around at least one adjacent portions of a leg of a person above or below the knee, the base having an exterior surface and an interior surface when worn; and
   (b) a spider member having a first upper tensioning strap, a second upper tensioning strap, a first lower tensioning strap, and a second lower tensioning strap,
   wherein the spider member is permanently fastened to the interior surface of the base, wherein the base has an aperture, and wherein at least one of the first upper tensioning strap, second upper tensioning strap, first lower tensioning strap, and second lower tensioning strap extends through the aperture when the brace is worn.

2. The knee brace of claim 1 wherein the base has a base central portion mid-line axis, wherein the spider member has a spider member central portion mid-line axis, and wherein the spider member is permanently fastened to the interior surface of the base by a plurality of stitches through at least a portion of the base central portion mid-line axis and through at least a portion of the spider member central portion mid-line axis.

3. The knee brace of claim 2 wherein the portion of the base central portion mid-line axis overlaps and aligns with the portion of the spider member central portion mid-line axis.

4. The knee brace of claim 1 wherein the base has a base kneecap opening, wherein the spider member has a spider member kneecap opening, and wherein the base kneecap opening is centered on the spider member kneecap opening when worn.

5. A knee brace, comprising:
   (a) a base wearable in snug covering relationship to portions of a knee to encircle at least one adjacent portions of a leg of a person above or below the knee, the base having an exterior surface and an interior surface when worn; and (b) a spider member having a first upper tensioning strap, a second upper tensioning strap, a first lower tensioning strap, and a second lower tensioning strap, wherein the base has a base central portion mid-line axis, wherein the spider member has a spider member central portion mid-line axis, and wherein the spider member is permanently fastened to the base by a plurality of stitches through at least a portion of the base central portion mid-line axis and through at least a portion of the spider member central portion mid-line axis, wherein the base has an aperture, and wherein at least one of the first upper tensioning strap, second upper tensioning strap, first lower tensioning strap, and second lower tensioning strap extends through the aperture when the brace is worn.

6. The knee brace of claim 5 wherein the spider member is permanently fastened to the interior surface of the base.

7. The knee brace of claim 5 wherein the portion of the base central portion mid-line axis overlaps and aligns with the portion of the spider member central portion mid-line axis.

8. The knee brace of claim 5 wherein the spider member is not otherwise permanently fastened to the base.

9. A knee brace, comprising:
(a) a base wearable in snug covering relationship to portions of a knee to encircle at least one adjacent portions of a leg of a person above or below the knee, the base having an exterior surface and an interior surface when worn; and
(b) a shaped tensioning member formed of a material that is elastic in all directions and having a first upper tensioning strap, a second upper tensioning strap, a first lower tensioning strap, and a second lower tensioning strap,
wherein the shaped tensioning member is permanently fastened to the interior surface of the base, wherein the base has at least one aperture, and wherein at least one of the first upper tensioning strap, second upper tensioning strap, first lower tensioning strap, and second lower tensioning strap extends through the aperture when the brace is worn.

10. The knee brace of claim 9 wherein the at least one aperture of the base includes a first upper aperture, a second upper aperture, a first lower aperture, and a second lower aperture;
and wherein the first upper tensioning strap extends through the first upper aperture to a first free strap end, wherein the second upper tensioning strap extends through the second upper aperture to a second strap end, wherein the first lower tensioning strap extends through the first lower aperture to a third strap end, and wherein the second lower tensioning strap extends through the second lower aperture to a fourth strap end, and wherein the first strap end, the second strap end, the third strap end and the fourth strap end are detachably attachable to the exterior surface of the base when the brace is worn.

11. The knee brace of claim 10 further comprising an exterior mesh layer permanently fastened to at least one of the first upper tensioning strap, the second upper tensioning strap, the first lower tensioning strap, and the second lower tensioning strap.

12. The knee brace of claim 11 wherein the exterior mesh layer permanently fastened to the first upper tensioning strap near the first strap end, the second upper tensioning strap near the second strap end, the first lower tensioning strap near the third strap end, and the second lower tensioning strap near the fourth strap end.

13. A knee brace, comprising:
(a) a base wearable in snug covering relationship to portions of a knee to extend all the way around at least one adjacent portions of a leg of a person above or below the knee, the base having an exterior surface and an interior surface when worn; and
(b) a spider member having a plurality of tensioning straps, and
wherein a portion of the spider member is positioned between the base and the leg of the person when worn, wherein the base has an aperture, and wherein at least one of the tensioning straps in the plurality of tensioning straps extends through the aperture when the brace is worn.

14. The knee brace of claim 13 wherein the plurality of tensioning straps comprises a first upper tensioning strap, a second upper tensioning strap, a first lower tensioning strap, and a second lower tensioning strap.

15. The knee brace of claim 13 wherein the base includes a plurality of apertures, and wherein each tensioning strap in the plurality of tensioning straps extends through at least one aperture in the plurality of apertures.

16. A knee brace, comprising:
(a) a base wearable in snug covering relationship to portions of a knee to encircle at least one adjacent portions of a leg of a person above or below the knee, the base having an exterior surface and an interior surface when worn; and
(b) a spider member having a first upper tensioning strap, a second upper tensioning strap, a first lower tensioning strap, and a second lower tensioning strap,
wherein a portion of the spider member is positioned between the base and the leg of the person when worn, wherein the base has at least one aperture, and wherein at least one of the first upper tensioning strap, second upper tensioning strap, first lower tensioning strap, and second lower tensioning strap extends through the aperture when the brace is worn.

17. The knee brace of claim 16 wherein the base has a base central portion, wherein the spider member has a spider member central portion, and wherein the spider member is permanently fastened to the base at a point, where the point is located in the base central portion and the point is located in the spider member central portion.

18. The knee brace of claim 16 wherein the base has a base central portion, wherein the spider member has a spider member central portion, wherein the spider member is permanently fastened to the base at a plurality of points, and wherein the plurality of points are located in the base central portion and the plurality of points are located in the spider member central portion.

19. The knee brace of claim 18 wherein the plurality of points fall along a line.

20. The knee brace of claim 19 wherein the base has a mid-line axis, and wherein the line falls along the mid-line axis.

* * * * *